(12) United States Patent
Braido

(10) Patent No.: US 9,820,851 B2
(45) Date of Patent: Nov. 21, 2017

(54) COLLAPSIBLE-EXPANDABLE PROSTHETIC HEART VALVES WITH STRUCTURES FOR CLAMPING NATIVE TISSUE

(71) Applicant: St. Jude Medical, LLC, Abbott Park, IL (US)

(72) Inventor: Peter N. Braido, Wyoming, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 0 days.

(21) Appl. No.: 14/688,415

(22) Filed: Apr. 16, 2015

(65) Prior Publication Data
US 2015/0216658 A1    Aug. 6, 2015

Related U.S. Application Data

(63) Continuation of application No. 11/906,133, filed on Sep. 28, 2007.

(51) Int. Cl.
*A61F 2/24*    (2006.01)

(52) U.S. Cl.
CPC .............. *A61F 2/24* (2013.01); *A61F 2/2409* (2013.01); *A61F 2/2418* (2013.01);
(Continued)

(58) Field of Classification Search
CPC .... A61F 2/2475; A61F 2/2412; A61F 2/2418; A61F 2250/0039; A61F 2250/0003; A61F 2/24; A61F 2220/0008; A61F 2230/005; A61F 2230/0054; A61F 2230/0078; A61F 2/2409; A61F 2/2433; A61F 2/844;
(Continued)

(56) References Cited

U.S. PATENT DOCUMENTS

| 3,409,013 A | 11/1968 | Berry |
| 3,467,102 A | 9/1969 | Fogarty et al. |

(Continued)

FOREIGN PATENT DOCUMENTS

| DE | 2246526 | 3/1973 |
| DE | 19532846 | 3/1997 |

(Continued)

OTHER PUBLICATIONS

78. Heart repairs without surgery. Minimally invasive procedures aim to correct valve leakage. PubMed ID 15586429, Heart Advisor, Sep. 2004.

(Continued)

*Primary Examiner* — Thomas J Sweet
*Assistant Examiner* — Seema Mathew
(74) *Attorney, Agent, or Firm* — Lerner, David, Littenberg, Krumholz & Mentlik, LLP

(57) ABSTRACT

A prosthetic heart valve is designed to be circumferentially collapsible for less invasive delivery into the patient. At the implant site the valve re-expands to a larger circumferential size, i.e., the size that it has for operation as a replacement for one of the patient's native heart valves. The valve includes structures that, at the implant site, extend radially outwardly to engage tissue structures above and below the native heart valve annulus. These radially outwardly extending structures clamp the native tissue between them and thereby help to anchor the prosthetic valve at the desired location in the patient.

26 Claims, 18 Drawing Sheets

(52) U.S. Cl.
CPC .......... *A61F 2/2433* (2013.01); *A61F 2/2412* (2013.01); *A61F 2220/0008* (2013.01); *A61F 2230/005* (2013.01); *A61F 2230/0054* (2013.01); *A61F 2230/0078* (2013.01)

(58) Field of Classification Search
CPC .......... A61F 2/848; A61F 2/852; A61F 2/856; A61F 2/93; A61F 2/954; A61F 2/962; A61F 2/966; A61F 2/04; A61F 2/86; A61F 2/90; A61F 2/44; A61F 2230/0069
See application file for complete search history.

(56) References Cited

U.S. PATENT DOCUMENTS

| | | | |
|---|---|---|---|
| 3,548,417 A | 12/1970 | Kischer | |
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 3,983,581 A | 10/1976 | Angell et al. | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,275,469 A | 6/1981 | Gabbay | |
| 4,297,749 A | 11/1981 | Davis et al. | |
| RE30,912 E | 4/1982 | Hancock | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,470,157 A | 9/1984 | Love | |
| 4,491,986 A | 1/1985 | Gabbay | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,796,629 A | 1/1989 | Grayzel | |
| 4,797,901 A | 1/1989 | Goeme et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,258,023 A | 11/1993 | Reger | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane | |
| 5,411,552 A | 5/1995 | Andersen et al. | |
| 5,415,667 A | 5/1995 | Frater | |
| 5,443,446 A | 8/1995 | Shturman | |
| 5,480,423 A | 1/1996 | Ravenscroft et al. | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,571,175 A | 11/1996 | Vanney et al. | |
| 5,591,185 A | 1/1997 | Kilmer et al. | |
| 5,607,464 A | 3/1997 | Trescony et al. | |
| 5,609,626 A | 3/1997 | Quijano et al. | |
| 5,628,786 A | 5/1997 | Banas et al. | |
| 5,639,274 A | 6/1997 | Fischell et al. | |
| 5,665,115 A | 9/1997 | Cragg | |
| 5,693,088 A | 12/1997 | Lazarus | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,769,882 A | 6/1998 | Fogarty et al. | |
| 5,776,188 A | 7/1998 | Shepherd et al. | |
| 5,800,508 A | 9/1998 | Goicoechea et al. | |
| 5,840,081 A | 11/1998 | Andersen et al. | |
| 5,843,161 A | 12/1998 | Solovay | |
| 5,843,167 A | 12/1998 | Dwyer et al. | |
| 5,855,597 A | 1/1999 | Jayaraman | |
| 5,855,601 A * | 1/1999 | Bessler .......... | A61B 17/320725 623/2.38 |
| 5,855,602 A | 1/1999 | Angell | |
| 5,925,063 A | 7/1999 | Khosravi | |
| 5,928,281 A | 7/1999 | Huynh et al. | |
| 5,935,163 A | 8/1999 | Gabbay | |
| 5,957,949 A | 9/1999 | Leonhardt et al. | |
| 5,961,549 A | 10/1999 | Nguyen et al. | |
| 6,015,431 A | 1/2000 | Thornton et al. | |
| 6,027,525 A | 2/2000 | Suh et al. | |
| 6,045,576 A | 4/2000 | Starr et al. | |
| 6,077,297 A | 6/2000 | Robinson et al. | |
| 6,083,257 A | 7/2000 | Taylor et al. | |
| 6,090,140 A | 7/2000 | Gabbay | |
| 6,110,198 A | 8/2000 | Fogarty et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,174,327 B1 | 1/2001 | Mertens et al. | |
| 6,210,408 B1 | 4/2001 | Chandrasekaran et al. | |
| 6,214,036 B1 | 4/2001 | Letendre et al. | |
| 6,217,585 B1 | 4/2001 | Houser et al. | |
| 6,221,091 B1 | 4/2001 | Khosravi | |
| 6,231,602 B1 | 5/2001 | Carpentier et al. | |
| 6,245,102 B1 | 6/2001 | Jayaraman | |
| 6,264,691 B1 | 7/2001 | Gabbay | |
| 6,267,783 B1 | 7/2001 | Letendre et al. | |
| 6,299,637 B1 | 10/2001 | Shaolian et al. | |
| 6,302,906 B1 | 10/2001 | Goicoechea et al. | |
| 6,306,164 B1 | 10/2001 | Kujawski | |
| 6,312,465 B1 | 11/2001 | Griffin et al. | |
| 6,350,277 B1 | 2/2002 | Kocur | |
| 6,352,554 B2 | 3/2002 | De Paulis | |
| 6,368,348 B1 | 4/2002 | Gabbay | |
| 6,419,695 B1 | 7/2002 | Gabbay | |
| 6,425,916 B1 | 7/2002 | Garrison et al. | |
| 6,440,164 B1 | 8/2002 | DiMatteo et al. | |
| 6,454,799 B1 | 9/2002 | Schreck | |
| 6,458,153 B1 | 10/2002 | Bailey et al. | |

(56) References Cited

U.S. PATENT DOCUMENTS

| | | | |
|---|---|---|---|
| 6,461,382 B1 | 10/2002 | Cao |
| 6,468,660 B2 | 10/2002 | Ogle et al. |
| 6,482,228 B1 | 11/2002 | Norred |
| 6,488,702 B1 | 12/2002 | Besselink |
| 6,488,704 B1 | 12/2002 | Connelly et al. |
| 6,517,576 B2 | 2/2003 | Gabbay |
| 6,533,810 B2 | 3/2003 | Hankh et al. |
| 6,569,196 B1 | 5/2003 | Vesely |
| 6,582,462 B1 | 6/2003 | Andersen et al. |
| 6,582,464 B2 | 6/2003 | Gabbay |
| 6,605,112 B1 | 8/2003 | Moll et al. |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,712,836 B1 | 3/2004 | Berg et al. |
| 6,716,244 B2 | 4/2004 | Klaco |
| 6,719,789 B2 | 4/2004 | Cox |
| 6,726,715 B2 | 4/2004 | Sutherland |
| 6,729,356 B1 | 5/2004 | Baker et al. |
| 6,730,118 B2 | 5/2004 | Spenser et al. |
| 6,733,525 B2 | 5/2004 | Yang et al. |
| 6,767,362 B2 | 7/2004 | Schreck |
| 6,780,510 B2 | 8/2004 | Ogle et al. |
| 6,783,556 B1 | 8/2004 | Gabbay |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,814,754 B2 | 11/2004 | Greenhalgh |
| 6,830,584 B1 | 12/2004 | Seguin |
| 6,830,585 B1 | 12/2004 | Artof et al. |
| 6,837,902 B2 | 1/2005 | Nguyen et al. |
| 6,860,901 B1 | 3/2005 | Baker et al. |
| 6,869,444 B2 | 3/2005 | Gabbay |
| 6,875,231 B2 | 4/2005 | Anduiza et al. |
| 6,893,460 B2 | 5/2005 | Spenser et al. |
| 6,908,481 B2 | 6/2005 | Cribier |
| 6,911,040 B2 | 6/2005 | Johnson et al. |
| 6,951,573 B1 | 10/2005 | Dilling |
| 7,018,406 B2 | 3/2006 | Seguin et al. |
| 7,018,408 B2 | 3/2006 | Bailey et al. |
| 7,025,780 B2 | 4/2006 | Gabbay |
| 7,041,132 B2 | 5/2006 | Quijano et al. |
| 7,044,966 B2 | 5/2006 | Svanidze et al. |
| 7,101,396 B2 | 9/2006 | Artof et al. |
| 7,137,184 B2 | 11/2006 | Schreck |
| 7,147,663 B1 | 12/2006 | Berg et al. |
| 7,160,322 B2 | 1/2007 | Gabbay |
| 7,195,641 B2 | 3/2007 | Palmaz et al. |
| 7,198,646 B2 | 4/2007 | Figulla et al. |
| 7,201,772 B2 | 4/2007 | Schwammenthal et al. |
| 7,247,167 B2 | 7/2007 | Gabbay |
| 7,252,682 B2 | 8/2007 | Seguin |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,276,084 B2 | 10/2007 | Yang et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,331,991 B2 | 2/2008 | Kheradvar et al. |
| 7,338,520 B2 | 3/2008 | Bailey et al. |
| 7,374,571 B2 | 5/2008 | Pease et al. |
| 7,374,573 B2 | 5/2008 | Gabbay |
| 7,381,218 B2 | 6/2008 | Schreck |
| 7,381,219 B2 | 6/2008 | Salahieh et al. |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,462,191 B2 | 12/2008 | Spenser et al. |
| 7,481,838 B2 | 1/2009 | Carpentier et al. |
| 7,510,572 B2 | 3/2009 | Gabbay |
| 7,510,575 B2 | 3/2009 | Spenser et al. |
| 7,524,331 B2 | 4/2009 | Birdsall |
| 7,527,647 B2 | 5/2009 | Spence |
| 7,530,995 B2 | 5/2009 | Quijano et al. |
| 7,534,261 B2 | 5/2009 | Friedman |
| RE40,816 E | 6/2009 | Taylor et al. |
| 7,585,321 B2 | 9/2009 | Cribier |
| 7,597,711 B2 | 10/2009 | Drews et al. |
| 7,628,805 B2 | 12/2009 | Spenser et al. |
| 7,682,390 B2 | 3/2010 | Seguin |
| 7,708,775 B2 | 5/2010 | Rowe et al. |
| 7,717,955 B2 * | 5/2010 | Lane ............... A61F 2/2409 623/2.14 |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,871,435 B2 | 1/2011 | Carpentier et al. |
| 7,892,281 B2 | 2/2011 | Seguin et al. |
| 7,914,569 B2 | 3/2011 | Nguyen et al. |
| 7,951,197 B2 | 5/2011 | Lane et al. |
| 7,959,666 B2 | 6/2011 | Salahieh et al. |
| 7,959,672 B2 | 6/2011 | Salahieh et al. |
| 7,959,674 B2 | 6/2011 | Shu et al. |
| 7,967,857 B2 | 6/2011 | Lane |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| 8,083,793 B2 | 12/2011 | Lane et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,226,710 B2 | 7/2012 | Nguyen et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,349,000 B2 | 1/2013 | Schreck |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| 8,454,685 B2 | 6/2013 | Hariton et al. |
| 8,454,686 B2 | 6/2013 | Alkhatib |
| 8,465,540 B2 | 6/2013 | Straubinger et al. |
| 8,500,798 B2 | 8/2013 | Rowe et al. |
| 8,512,396 B2 | 8/2013 | Styrc |

(56) References Cited

U.S. PATENT DOCUMENTS

| | | |
|---|---|---|
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,673,000 B2 | 3/2014 | Tabor et al. |
| 8,685,080 B2 | 4/2014 | White |
| 8,685,086 B2 | 4/2014 | Navia et al. |
| 8,728,154 B2 | 5/2014 | Alkhatib |
| 8,747,459 B2 | 6/2014 | Nguyen et al. |
| 8,747,460 B2 | 6/2014 | Tuval et al. |
| 8,764,820 B2 | 7/2014 | Dehdashtian et al. |
| 8,771,345 B2 | 7/2014 | Tuval et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,663 B2 | 9/2014 | Salahieh et al. |
| 8,845,721 B2 | 9/2014 | Braido et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2* | 2/2015 | Bonyuet ............... A61F 2/2415 623/2.1 |
| 8,961,595 B2 | 2/2015 | Alkhatib |
| 8,974,523 B2 | 3/2015 | Thill et al. |
| 8,974,524 B2 | 3/2015 | Yeung et al. |
| 8,992,608 B2 | 3/2015 | Haug et al. |
| 9,168,129 B2* | 10/2015 | Valdez ............... A61F 2/2412 |
| 9,186,249 B2 | 11/2015 | Rolando et al. |
| 9,308,087 B2* | 4/2016 | Lane ............... A61F 2/2403 |
| 9,393,110 B2 | 7/2016 | Levi et al. |
| 2001/0007956 A1 | 7/2001 | Letac et al. |
| 2001/0010017 A1 | 7/2001 | Letac et al. |
| 2001/0027338 A1 | 10/2001 | Greenberg |
| 2001/0041928 A1 | 11/2001 | Pavcnik et al. |
| 2002/0032481 A1 | 3/2002 | Gabbay |
| 2002/0036220 A1 | 3/2002 | Gabbay |
| 2002/0138138 A1 | 9/2002 | Yang |
| 2002/0173842 A1 | 11/2002 | Buchanan |
| 2003/0023303 A1 | 1/2003 | Palmaz et al. |
| 2003/0027332 A1 | 2/2003 | Lafrance et al. |
| 2003/0036791 A1 | 2/2003 | Philipp et al. |
| 2003/0040792 A1 | 2/2003 | Gabbay |
| 2003/0050694 A1 | 3/2003 | Yang et al. |
| 2003/0100939 A1 | 5/2003 | Yodfat et al. |
| 2003/0109924 A1 | 6/2003 | Cribier |
| 2003/0114913 A1 | 6/2003 | Spenser et al. |
| 2003/0130726 A1 | 7/2003 | Thorpe et al. |
| 2003/0167089 A1* | 9/2003 | Lane ............... A61F 2/2412 623/2.14 |
| 2003/0199963 A1 | 10/2003 | Tower et al. |
| 2003/0199971 A1 | 10/2003 | Tower et al. |
| 2003/0212454 A1 | 11/2003 | Scott et al. |
| 2003/0236567 A1 | 12/2003 | Elliot |
| 2003/0236568 A1 | 12/2003 | Hojeibane et al. |
| 2004/0033364 A1 | 2/2004 | Spiridigliozzi et al. |
| 2004/0039436 A1 | 2/2004 | Spenser et al. |
| 2004/0049262 A1 | 3/2004 | Obermiller et al. |
| 2004/0082989 A1 | 4/2004 | Cook et al. |
| 2004/0093075 A1 | 5/2004 | Kuehne |
| 2004/0111111 A1 | 6/2004 | Lin |
| 2004/0186565 A1 | 9/2004 | Schreck |
| 2004/0210304 A1 | 10/2004 | Seguin et al. |
| 2004/0260389 A1 | 12/2004 | Case et al. |
| 2005/0033398 A1 | 2/2005 | Seguin |
| 2005/0043790 A1 | 2/2005 | Seguin |
| 2005/0075718 A1 | 4/2005 | Nguyen et al. |
| 2005/0075725 A1 | 4/2005 | Rowe |
| 2005/0096726 A1 | 5/2005 | Sequin et al. |
| 2005/0113910 A1 | 5/2005 | Paniagua et al. |
| 2005/0137682 A1* | 6/2005 | Justino ............... A61F 2/2412 623/1.24 |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2005/0165477 A1 | 7/2005 | Anduiza et al. |
| 2005/0177228 A1 | 8/2005 | Solem et al. |
| 2005/0192665 A1 | 9/2005 | Spenser et al. |
| 2005/0197695 A1 | 9/2005 | Stacchino et al. |
| 2005/0203605 A1 | 9/2005 | Dolan |
| 2005/0203616 A1 | 9/2005 | Cribier |
| 2005/0234546 A1 | 10/2005 | Nugent et al. |
| 2005/0251251 A1 | 11/2005 | Cribier |
| 2005/0256566 A1 | 11/2005 | Gabbay |
| 2005/0283231 A1 | 12/2005 | Haug et al. |
| 2006/0004439 A1 | 1/2006 | Spenser et al. |
| 2006/0004442 A1 | 1/2006 | Spenser et al. |
| 2006/0008497 A1 | 1/2006 | Gabbay |
| 2006/0025855 A1* | 2/2006 | Lashinski ............... A61F 2/2436 623/2.1 |
| 2006/0025857 A1 | 2/2006 | Bergheim et al. |
| 2006/0052867 A1 | 3/2006 | Revuelta et al. |
| 2006/0058872 A1 | 3/2006 | Salahieh et al. |
| 2006/0074484 A1* | 4/2006 | Huber ............... A61B 17/22004 623/2.11 |
| 2006/0122692 A1 | 6/2006 | Gilad et al. |
| 2006/0129235 A1 | 6/2006 | Seguin et al. |
| 2006/0149350 A1 | 7/2006 | Patel et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178731 A1 | 8/2006 | Tower |
| 2006/0178740 A1 | 8/2006 | Stacchino et al. |
| 2006/0195183 A1 | 8/2006 | Navia et al. |
| 2006/0195186 A1 | 8/2006 | Drews et al. |
| 2006/0206202 A1 | 9/2006 | Bonhoeffer et al. |
| 2006/0229719 A1 | 10/2006 | Marquez et al. |
| 2006/0241744 A1 | 10/2006 | Beith |
| 2006/0241745 A1 | 10/2006 | Solem |
| 2006/0253191 A1 | 11/2006 | Salahieh et al. |
| 2006/0259120 A1 | 11/2006 | Vongphakdy et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2006/0287719 A1* | 12/2006 | Rowe ............... A61F 2/2409 623/2.18 |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0050021 A1 | 3/2007 | Johnson |
| 2007/0055358 A1 | 3/2007 | Krolik et al. |
| 2007/0067029 A1 | 3/2007 | Gabbay |
| 2007/0073387 A1 | 3/2007 | Forster et al. |
| 2007/0093890 A1 | 4/2007 | Eliasen et al. |
| 2007/0100435 A1 | 5/2007 | Case et al. |
| 2007/0112355 A1 | 5/2007 | Salahieh et al. |
| 2007/0112422 A1 | 5/2007 | Dehdashtian |
| 2007/0118210 A1 | 5/2007 | Pinchuk |
| 2007/0118214 A1 | 5/2007 | Salahieh et al. |
| 2007/0142907 A1 | 6/2007 | Moaddeb et al. |
| 2007/0162100 A1 | 7/2007 | Gabbay |
| 2007/0162107 A1 | 7/2007 | Haug et al. |

(56) References Cited

U.S. PATENT DOCUMENTS

| | | |
|---|---|---|
| 2007/0203503 A1 | 8/2007 | Salahieh et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0239265 A1 | 10/2007 | Birdsall |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0255398 A1 | 11/2007 | Yang et al. |
| 2007/0270944 A1 | 11/2007 | Bergheim et al. |
| 2007/0288087 A1 | 12/2007 | Fearnot et al. |
| 2008/0021546 A1 | 1/2008 | Patz et al. |
| 2008/0021552 A1 | 1/2008 | Gabbay |
| 2008/0039934 A1 | 2/2008 | Styrc |
| 2008/0071361 A1 | 3/2008 | Tuval et al. |
| 2008/0071369 A1 | 3/2008 | Tuval et al. |
| 2008/0077236 A1 | 3/2008 | Letac et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0208327 A1 | 8/2008 | Rowe |
| 2008/0208329 A1* | 8/2008 | Bishop ............... A61B 17/10 623/2.11 |
| 2008/0243245 A1 | 10/2008 | Thambar et al. |
| 2008/0243246 A1 | 10/2008 | Ryan et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0171447 A1 | 7/2009 | Von Segesser et al. |
| 2009/0192599 A1 | 7/2009 | Lane et al. |
| 2009/0248149 A1 | 10/2009 | Gabbay |
| 2009/0264997 A1 | 10/2009 | Salahieh et al. |
| 2009/0276027 A1 | 11/2009 | Glynn |
| 2009/0287296 A1 | 11/2009 | Manasse |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0082094 A1 | 4/2010 | Quadri et al. |
| 2010/0087907 A1 | 4/2010 | Lattouf |
| 2010/0100176 A1 | 4/2010 | Elizondo et al. |
| 2010/0114305 A1* | 5/2010 | Kang ............... A61F 2/2418 623/2.1 |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1* | 7/2010 | Toomes ............... A61F 2/2418 623/2.18 |
| 2010/0185277 A1 | 7/2010 | Braido et al. |
| 2010/0191326 A1 | 7/2010 | Alkhatib |
| 2010/0204781 A1* | 8/2010 | Alkhatib ............... A61F 2/2418 623/1.26 |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0262231 A1 | 10/2010 | Tuval et al. |
| 2010/0286768 A1 | 11/2010 | Alkhatib |
| 2010/0298931 A1 | 11/2010 | Quadri et al. |
| 2011/0022157 A1 | 1/2011 | Essinger et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1* | 4/2011 | Braido ............... A61F 2/2412 623/1.26 |
| 2011/0137397 A1 | 6/2011 | Chau et al. |
| 2011/0166636 A1 | 7/2011 | Rowe |
| 2011/0172765 A1 | 7/2011 | Nguyen et al. |
| 2011/0208283 A1 | 8/2011 | Rust |
| 2011/0264206 A1 | 10/2011 | Tabor |
| 2011/0282439 A1 | 11/2011 | Thill et al. |
| 2011/0301692 A1 | 12/2011 | Seguin |
| 2011/0319988 A1 | 12/2011 | Schankereli et al. |
| 2012/0035719 A1 | 2/2012 | Forster et al. |
| 2012/0035722 A1 | 2/2012 | Tuval |
| 2012/0046742 A1 | 2/2012 | Tuval et al. |
| 2012/0078347 A1 | 3/2012 | Braido et al. |
| 2012/0078357 A1 | 3/2012 | Conklin |
| 2012/0083878 A1 | 4/2012 | Sequin et al. |
| 2012/0083879 A1* | 4/2012 | Eberhardt ............. H01M 4/131 623/2.18 |
| 2012/0101572 A1 | 4/2012 | Kovalsky et al. |
| 2012/0123529 A1* | 5/2012 | Levi ............... A61F 2/2412 623/2.11 |
| 2012/0179244 A1 | 7/2012 | Schankereli et al. |
| 2012/0215303 A1 | 8/2012 | Quadri et al. |
| 2012/0232646 A1 | 9/2012 | Agathos |
| 2012/0271398 A1* | 10/2012 | Essinger ............... A61F 2/2412 623/1.11 |
| 2012/0277856 A1 | 11/2012 | Spenser et al. |
| 2012/0296418 A1 | 11/2012 | Bonyuet et al. |
| 2012/0303116 A1 | 11/2012 | Gorman, III et al. |
| 2012/0316642 A1 | 12/2012 | Yu et al. |
| 2013/0018458 A1 | 1/2013 | Yohanan et al. |
| 2013/0023984 A1 | 1/2013 | Conklin |
| 2013/0150956 A1 | 6/2013 | Yohanan et al. |
| 2013/0204359 A1 | 8/2013 | Thubrikar et al. |
| 2013/0211508 A1 | 8/2013 | Lane et al. |
| 2013/0218267 A1 | 8/2013 | Braido et al. |
| 2013/0274870 A1 | 10/2013 | Lombardi et al. |
| 2013/0274873 A1* | 10/2013 | Delaloye ............... A61F 2/2409 623/2.18 |
| 2013/0338765 A1 | 12/2013 | Braido et al. |
| 2013/0345786 A1* | 12/2013 | Behan ............... A61F 2/04 623/1.11 |
| 2014/0121763 A1 | 5/2014 | Duffy et al. |
| 2014/0142694 A1 | 5/2014 | Tabor et al. |
| 2014/0155997 A1 | 6/2014 | Braido |
| 2014/0194981 A1 | 7/2014 | Menk et al. |
| 2014/0214157 A1* | 7/2014 | Bortlein ............... A61F 2/2418 623/2.11 |
| 2014/0214159 A1 | 7/2014 | Vidlund et al. |
| 2014/0228946 A1 | 8/2014 | Chau et al. |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350663 A1 | 11/2014 | Braido et al. |
| 2014/0350665 A1 | 11/2014 | Braido et al. |
| 2014/0350667 A1 | 11/2014 | Braido et al. |
| 2014/0350668 A1* | 11/2014 | Delaloye ............... A61F 2/95 623/2.17 |
| 2014/0350669 A1 | 11/2014 | Gillespie et al. |
| 2015/0216658 A1* | 8/2015 | Braido ............... A61F 2/2418 623/2.13 |
| 2015/0320556 A1* | 11/2015 | Levi ............... A61F 2/2427 623/2.11 |
| 2016/0354201 A1* | 12/2016 | Keogh ............... A61F 2/2418 |

FOREIGN PATENT DOCUMENTS

| | | |
|---|---|---|
| DE | 19546692 A1 | 6/1997 |
| DE | 19857887 A1 | 7/2000 |
| DE | 19907646 | 8/2000 |
| DE | 10049812 | 4/2002 |
| DE | 10049813 | 4/2002 |
| DE | 10049814 | 4/2002 |
| DE | 10049815 | 4/2002 |
| DE | 10121210 A1 | 11/2002 |
| DE | 202008009610 U1 | 12/2008 |
| EP | 0103546 | 3/1984 |
| EP | 0144167 | 6/1985 |
| EP | 0592410 | 4/1994 |
| EP | 0850607 A1 | 7/1998 |

(56) References Cited

FOREIGN PATENT DOCUMENTS

| | | |
|---|---|---|
| EP | 0597967 B1 | 12/1999 |
| EP | 1000590 A1 | 5/2000 |
| EP | 1057460 A1 | 12/2000 |
| EP | 1088529 | 4/2001 |
| EP | 1360942 A1 | 11/2003 |
| EP | 1570809 A1 | 9/2005 |
| EP | 1584306 A1 | 10/2005 |
| EP | 1598031 A2 | 11/2005 |
| EP | 1926455 A2 | 6/2008 |
| EP | 2047824 A1 | 4/2009 |
| EP | 2059192 B1 | 5/2009 |
| EP | 2254513 A1 | 12/2010 |
| EP | 2537487 A1 | 12/2012 |
| EP | 2620125 A1 | 7/2013 |
| EP | 2749254 A1 | 7/2014 |
| EP | 2815725 A1 | 12/2014 |
| FR | 2788217 A1 | 7/2000 |
| FR | 2847800 A1 | 6/2004 |
| FR | 2850008 A1 | 7/2004 |
| GB | 2056023 | 3/1981 |
| JP | 2008541865 A | 11/2008 |
| JP | 2011500241 A | 1/2011 |
| JP | 2011522634 A | 8/2011 |
| JP | 2011528256 A | 11/2011 |
| JP | 2012504031 A | 2/2012 |
| SU | 158988 | 11/1963 |
| SU | 1271508 | 11/1986 |
| SU | 1371700 | 2/1988 |
| SU | 1457921 A1 | 2/1989 |
| WO | 9117720 A1 | 11/1991 |
| WO | 9217118 | 10/1992 |
| WO | 9301768 B1 | 2/1993 |
| WO | 9716133 A1 | 5/1997 |
| WO | 9724080 A1 | 7/1997 |
| WO | 9832412 A2 | 7/1998 |
| WO | 199829057 A1 | 7/1998 |
| WO | 9913801 A1 | 3/1999 |
| WO | 9933414 | 7/1999 |
| WO | 9940964 | 8/1999 |
| WO | 9947075 | 9/1999 |
| WO | 0018333 A1 | 4/2000 |
| WO | 200041652 A1 | 7/2000 |
| WO | 200047139 A1 | 8/2000 |
| WO | 0128459 A1 | 4/2001 |
| WO | 0135878 A2 | 5/2001 |
| WO | 0149213 A2 | 7/2001 |
| WO | 200149213 A2 | 7/2001 |
| WO | 0154624 A1 | 8/2001 |
| WO | 0154625 A1 | 8/2001 |
| WO | 0156500 A2 | 8/2001 |
| WO | 200162189 A1 | 8/2001 |
| WO | 2001054625 A1 | 8/2001 |
| WO | 0164137 | 9/2001 |
| WO | 0166035 A2 | 9/2001 |
| WO | 0166037 A2 | 9/2001 |
| WO | 0176510 A2 | 10/2001 |
| WO | 0222054 | 3/2002 |
| WO | 0236048 A1 | 5/2002 |
| WO | 0241789 | 5/2002 |
| WO | 0243620 | 6/2002 |
| WO | 0247575 A2 | 6/2002 |
| WO | 0249540 | 6/2002 |
| WO | 03037222 A2 | 5/2003 |
| WO | 03047468 A1 | 6/2003 |
| WO | 2003047468 A1 | 6/2003 |
| WO | 03075799 A1 | 9/2003 |
| WO | 2004016200 A1 | 2/2004 |
| WO | 2005062980 A2 | 7/2005 |
| WO | 2005087140 A1 | 9/2005 |
| WO | 2006014233 A2 | 2/2006 |
| WO | 2006034008 A2 | 3/2006 |
| WO | 2006041505 A1 | 4/2006 |
| WO | 2006073626 A2 | 7/2006 |
| WO | 2006124649 A2 | 11/2006 |
| WO | 2006127765 A1 | 11/2006 |
| WO | 2006128193 A2 | 11/2006 |
| WO | 2007053243 A2 | 5/2007 |
| WO | 2007071436 A2 | 6/2007 |
| WO | 2007/081820 A1 | 7/2007 |
| WO | 2008005405 A2 | 1/2008 |
| WO | 2008035337 A2 | 3/2008 |
| WO | 2008070797 A2 | 6/2008 |
| WO | 2008100600 A1 | 8/2008 |
| WO | 2008147964 A1 | 12/2008 |
| WO | 2008150529 A1 | 12/2008 |
| WO | 2009024859 A2 | 2/2009 |
| WO | 2009042196 A2 | 4/2009 |
| WO | 2009045338 A1 | 4/2009 |
| WO | 2009053497 A1 | 4/2009 |
| WO | 2009061389 A2 | 5/2009 |
| WO | 2009149462 A2 | 12/2009 |
| WO | 2010008548 A2 | 1/2010 |
| WO | 2010008549 A1 | 1/2010 |
| WO | 2010037141 A1 | 4/2010 |
| WO | 2010096176 A1 | 8/2010 |
| WO | 2010098857 A1 | 9/2010 |
| WO | 2010141847 A1 | 12/2010 |
| WO | 2011057087 A1 | 5/2011 |
| WO | 2012032187 A1 | 3/2012 |
| WO | 2012161786 A1 | 11/2012 |

OTHER PUBLICATIONS

Buellesfeld et al., Treatment of paravalvular leaks through inverventional techniques; Department of Cardiology, Ben University Hospital 2011.

Catheter-implanted prosthetic heart valves, Knudsen, L.L., et al., The International Journal of Artificial Organs, vol. 16, No. 5 1993, pp. 253-262.

De Cicco, Giuseppe, et al. "Aortic valve periprosthetic leakage: anatomic observations and surgical results." The Annals of thoracic surgery 79.5 (2005): 1480-1485.

Gössl, Mario, and Charanjit S. Rihal. "Percutaneous treatment of aortic and mitral valve paravalvular regurgitation." Current cardiology reports 15.8 (2013): 1-8.

International Search Report (dated Mar. 12, 2009), International Preliminary Report on Patentability (dated Mar. 30, 2010), and Written Opinion (dated Mar. 28, 2010), PCT/US2008/011188.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Maribeth et al., Transcatheter Umbrella Closure of Valvular and Paravalvular Leaks, Hourihan et al., Journal of the American College of Cardiology, vol. 20, No. 6, pp. 1371-1377, (1992).

Muñoz, Daniel Rodríguez, Carla Lázaro Rivera, and José Luis Zamorano Gómez. "Guidance of treatment of perivalvular prosthetic leaks." Current cardiology reports 16.1 (2014): 1-6.

Percutaneous aortic valve replacement: resection before implantation, 836-840, Quaden, Rene et al., European J. of Cardio-thoracic Surgery, 27 (2005).

Rohde, I., Masch, J.-M., Theisen-Kunde, D., Marczynski-Buhlow, M., Bombien Quaden, R., Lutter, G. and Brinkmann, R. (2015), Resection of Calcified Aortic Heart Leaflets In Vitro by Q-Switched 2? μm Microsecond Laser Radiation. Journal of Cardiac Surgery, 30: 157-162. doi: 10.1111/jocs.12481.

Ruiz, Carlos, Overview of PRE-CE Mark Transcatheter Aortic Valve Technologies, Euro PCR, dated May 25, 2010.

Swiatkiewicz, Iwona, et al. "Percutaneous closure of mitral perivalvular leak." Kardiologia polska 67.7 (2009): 762.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

U.S. Appl. No. 29/375,243, filed Sep. 20, 2010.

U.S. Appl. No. 29/375,260, filed Sep. 20, 2010.

Moazami et al., "Transluminal Aortic Valve Placement" (1996).

(56) References Cited

OTHER PUBLICATIONS

Bullesfeld et al., Percutaneous Implantation of the First Repositionable Aortic Valve Prosthesis in a Patient With Severe Aortic Stenosis, Catheterization & Cardiovascular Interventions 71:579-84 (2008).
Merriam Webster definition of "retard," www.merriam-webster.com/dictionary/retard.
Merriam Webster definition of "prevent," www.merriam-webstercom/dictionary/prevent.
Grube et al., "Percutaneous Implantation of the CoreValve Self-Expanding Valve Prosthesis in High-Risk Patients With Aortic Valve Disease" (2006).
Moazami et al., "Transluminal Aortic Valve Placement, a Feasibility Study With a Newly Collapsible Aortic Valve," (1996).
Evidence—Anlage 3 (Photograph).
International Search Report PCT/US2009/004094 dated Mar. 3, 2010.
Knudsen, L.L. et al., Catheter-implanted prosthetic heart valves, The International Journal of Artificial Organs, vol. 16, No. 5 1993, pp. 253-262.
Moazami, Nader et al., Transluminal Aortic Valve Placement, ASAIO Journal, 1996; 42:M381-M385.
Extended European Search Report for Application No. 14180622.4 dated Nov. 21, 2014.
Extended European Search Report for Application No. 14180625.7 dated Nov. 24, 2014.
Extended European Search Report for Application No. 14180623.2 dated Nov. 24, 2014.
Heat Advisor, "Heart repairs without surgery. Minimally invasive procedures aim to correct valve leakage", Sep. 2004, PubMed ID 15586429.
Hourihan, Maribeth et al., Transcatheter Umbrella Closure of Valvular and Paravalvular Leaks, Hourihan et al., Journal of the American College of Cardiology, vol. 20, No. 6, pp. 1371-1377, (1992).
European Communication for Application No. 09788918.2 dated Jun. 29, 2015.
International Search Report from corresponding PCT application No. PCT/US2011/054973 dated Apr. 23, 2012.
Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.
Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Serruys, P.W., et al., "Stenting of Coronary Arteries. Are we the Sorcerer's Apprentice?," European Heart Journal (1989) 10, 774-782, pp. 37-45, Jun. 13, 1989.
Kolata, Gina, "Device That Opens Clogged Arteries Gets a Failing Grade in a New Study," nytimes.com, http://www.nytimes.com/1991/01/03/healthidevice-that-opens-clogged-arteri-   es-gets-a-faili . . . , Jul. 29, 2009, 2 pages.
Urban, M.D., Philip, "Coronary Artery Stenting," Editions Medecine et Hygiene, Geneve, 1991, pp. 5-47.
Al-Khaja, N., et al., "Eleven Years' Experience with Carpentier-Edwards Biological Valves in Relation to Survival and complications," European Journal of Cardiothoracic Surgery 3:305-311, Jun. 30, 2009.
Wheatley, M.D., David J., "Valve Prostheses," Rob & Smith's Operative Surgery, Fourth Edition, pp. 415-424, Butterworths 1986.
Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62. cited by applicant.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.
Uchida, Barry T., et al., "Modifications of Gianturco Expandable Wire Stents," AJR:150, May 1988, Dec. 3, 1987, pp. 1185-1187.
Selby, M.D., J. Bayne, "Experience with New Retrieval Forceps for Foreign Body Removal in the Vascular, Urinary, and Biliary Systems," Radiology 1990; 176:535-538.
Inoune, M.D., Kanji et al., "Clinical Application of Transvenous Mitral Commissurotomy by a New Balloon Catheter," The Journal of Thoracic and Cardiovascular Surgery 87:394-402, 1984.
Al Zaibag, Muayed, et al., "Percutaneous Balloon Valvotomy in Tricuspid Stenosis," British Heart Journal, Jan. 1987, vol. 57, No. 1, pp. 51-53.
Lawrence, Jr., M.D., David D., "Percutaneous Endovascular Graft: Experimental Evaluation," Radiology 1897; 163: 357-360.
Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.
Sigwart, Ulrich, "An Overview of Intravascular Stents: Old and New," Chapter 48, Textbook of Interventional cardiology, 2nd Edition, W.B. Saunders Company, Philadelphia, PA, COPYRGT 1994, 1990, pp. 803-815.
Rashkind, M.D., William J., "Historical Aspects of Interventional Cardiology: Past, Present, Future," Texas Heart Institute Journal, Interventional Cardiology, pp. 363-367.
Rosch, M.D., Josef, "The Birth, Early Years and Future of Interventional Radiology," J Vasc Intery Radiol 2003; 14:841-853.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Ross, F.R.C.S., D.N., "Aortic Valve Surgery," Guy's Hospital, London, pp. 192-197, approximately 1968.
Rashkind, M.D., William J., "Creationof an Atrial Septal Defect Withoput Thoracotomy," the Journal of the American Medical Association, vol. 196, No. 11, Jun. 13, 1966, pp. 173-174.
Porstmann, W., et al., "Der Verschlu.beta. des Ductus Arteriosus Persistens ohne Thorakotomie," Thoraxchirurgie Vaskulare Chirurgie, Band 15, Heft 2, Stuttgart, im Apr. 1967, pp. 199-203, English translation of Abstract only.
Curriculum Vitae of Robert A. Ersek, M.D., FACS, Jul. 10, 2009, http://www.ersek.com/rae-cv.htm.
U.S. Appl. No. 13/572,842, filed Aug. 13, 2012, Kovalsky.
International Search Report and Written Opinion PCT/US2014/020872 dated Mar. 19, 2014.

* cited by examiner

US 9,820,851 B2

COLLAPSIBLE-EXPANDABLE PROSTHETIC HEART VALVES WITH STRUCTURES FOR CLAMPING NATIVE TISSUE

CROSS-REFERENCE TO RELATED APPLICATIONS

This application is a continuation of U.S. patent application Ser. No. 11/906,133, filed Sep. 28, 2007, the disclosure of which is hereby incorporated herein by reference.

BACKGROUND OF THE INVENTION

This invention relates to prosthetic heart valves, and more particularly to prosthetic heart valves that can be collapsed to a relatively small size for delivery into a patient and then re-expanded to full operating size at the final implant site in the patient.

At present there is considerable interest in prosthetic heart valves that can be collapsed to a relatively small circumferential (or annular perimeter) size for delivery into a patient (e.g., through tubular delivery apparatus like a catheter, a trocar, laparoscopic instrumentation, or the like). This is of interest because it can help to make replacement of a patient's defective heart valve less invasive for the patient. When the prosthetic valve reaches the desired implant site in the patient, the valve is re-expanded to a larger circumferential (or annular perimeter) size, which is the full operating size of the valve.

Because of the interest in prosthetic heart valves of the above general type, improvements to valves of this type are always being sought.

BRIEF SUMMARY OF THE INVENTION

In accordance with certain possible aspects of the invention, a prosthetic heart valve may include an annular structure that is annularly continuous and that has an annular perimeter that is changeable in length between (1) a first relatively small length suitable for delivery of the valve into a patient with reduced invasiveness, and (2) a second relatively large length suitable for use of the annular structure to engage tissue of the patient adjacent to the patient's native valve annulus and thereby implant the valve in the patient. The valve further includes a flexible leaflet structure attached to the annular structure. The annular structure may comprise an annular array of diamond-shaped cells. Upstream apex portions of at least some of these cells may be resiliently biased to deflect radially outwardly from at least some other portions of the annular structure, and downstream apex portions of at least some of these cells may also be resiliently biased to deflect radially outwardly from at least some other portions of the annular structure. As a result, when the valve is in use in a patient, tissue of the patient adjacent to the patient's native heart valve annulus is clamped between the upstream and downstream apex portions, with the upstream apex portions engaging tissue upstream from the annulus, and with the downstream apex portions engaging tissue downstream from the annulus.

In accordance with certain other possible aspects of the invention, a prosthetic aortic heart valve may include an annular structure that is annularly continuous and that has an annular perimeter that is changeable in length between (1) a first relatively small length suitable for delivery of the valve into a patient with reduced invasiveness, and (2) a second relatively large length suitable for use of the annular structure to engage tissue of the patient adjacent to the patient's native aortic valve annulus and also downstream from ostia of the patient's coronary arteries to thereby implant the valve in the patient. The annular structure may include an annularly continuous annulus portion adapted for implanting adjacent the patient's native aortic valve annulus upstream from the ostia of the patient's coronary arteries, and an annularly continuous aortic portion adapted for implanting in the patient's aorta downstream from those ostia. The annulus portion and the aortic portion are preferably connected to one another only by a plurality of linking structures that are disposed to pass through at least a portion of the patient's valsalva sinus at locations that are spaced from the ostia of the patient's coronary arteries in a direction that extends annularly around the valsalva sinus. The valve further includes a leaflet structure that is attached to the annulus portion. The annulus portion includes first and second tissue clamping structures that are spaced from one another along an axis that passes longitudinally through the valve, each of the clamping structures being resiliently biased to extend radially outwardly from the leaflet structure, whereby, in use, tissue of the patient adjacent to the patient's native aortic valve annulus is clamped between the first and second clamping structures, with the first clamping structure engaging tissue upstream from the annulus, and with the second clamping structure engaging tissue downstream from the annulus.

In accordance with certain still other possible aspects of the invention, a prosthetic aortic heart valve includes an annular structure that is annularly continuous and that has an annular perimeter that is changeable in length between (1) a first relatively small length suitable for delivery of the valve into a patient with reduced invasiveness, and (2) a second relatively large length suitable for use of the annular structure to engage tissue of the patient adjacent to the patient's native aortic valve annulus and thereby implant the valve in the patient. The valve further includes a flexible leaflet structure attached to the annular structure. When a valve having these aspects of the invention is implanted in the patient, any non-leaflet part of the valve that is at the level of the patient's native coronary artery ostia is confined in a direction that is circumferential of the valve to areas that are adjacent to the patient's native aortic valve commissures or downstream projections of those commissures, each of said areas having an extent in the circumferential direction that is less than the distance in the circumferential direction between circumferentially adjacent ones of those areas. In addition, the annular structure includes first and second tissue clamping structures that are spaced from one another along an axis that passes longitudinally through the valve. Each of the clamping structures is resiliently biased to extend radially outwardly from the leaflet structure, whereby, in use, tissue of the patient adjacent to the patient's native aortic valve annulus is clamped between the first and second clamping structures, with the first clamping structure engaging tissue upstream from the annulus, and with the second clamping structure engaging tissue downstream from the annulus.

Further features of the invention, its nature and various advantages, will be more apparent from the accompanying drawings and the following detailed description.

BRIEF DESCRIPTION OF THE DRAWINGS

FIG. 4 shows the depicted apparatus in its collapsed/pre-expanded state, and as though cut along a vertical line and then laid out flat.

DETAILED DESCRIPTION

Figure 1:
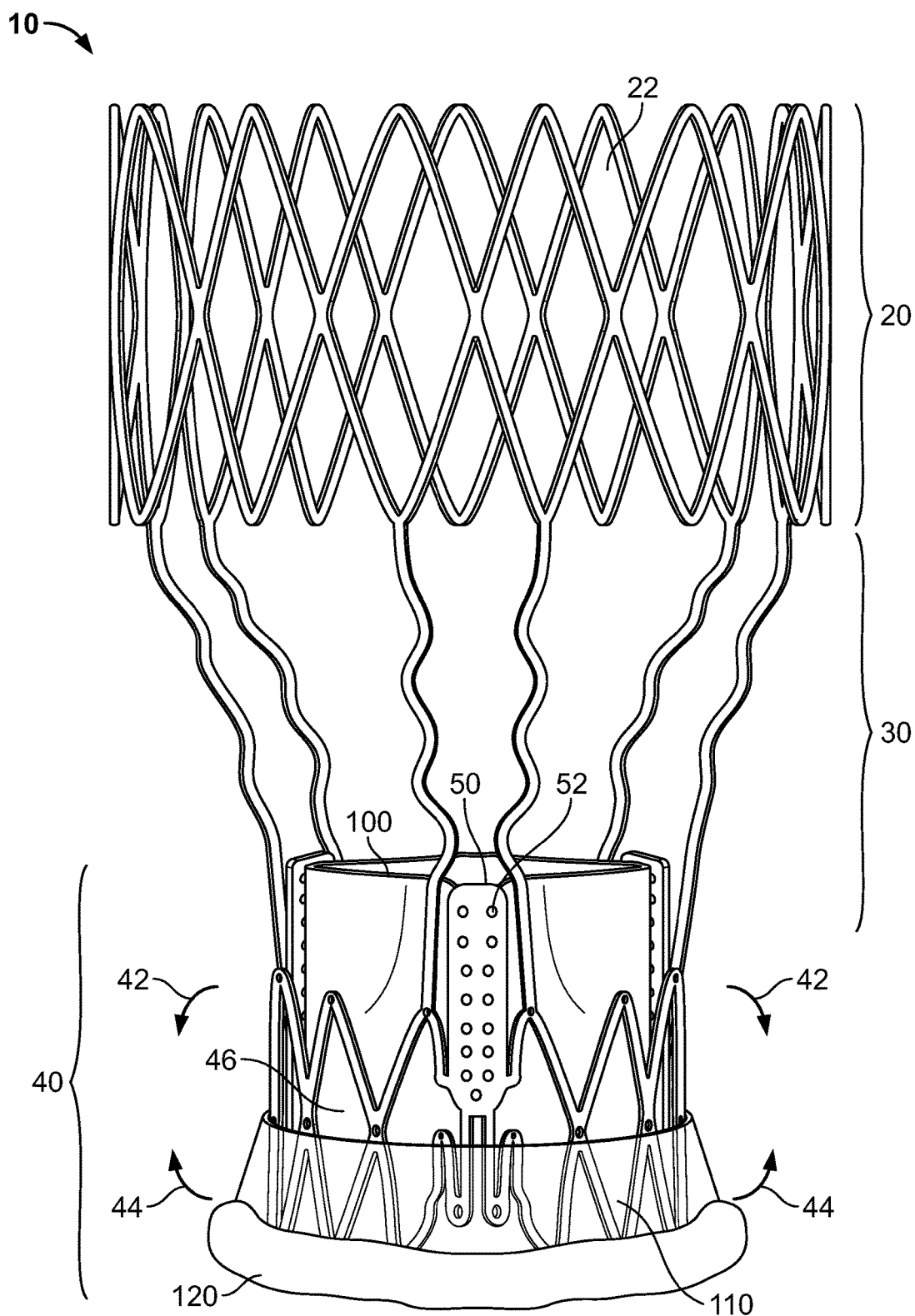
FIG. 1 is an elevational view of some components of an illustrative prosthetic valve in accordance with the invention.

Certain components of an illustrative embodiment of a prosthetic heart valve 10 in accordance with the invention are shown in FIG. 1. Valve 10 is designed for use as a replacement for a patient's native aortic valve. (Other valve types will be considered later in this specification.) FIG. 1 shows valve 10 in its expanded condition, i.e., the condition that the valve has when implanted in the patient. The depiction of valve 10 that is provided in FIG. 1 may omit certain components that the valve may have, but to some extent this is done to better reveal the components that are depicted in FIG. 1. More information will be provided about these possibly omitted components later in this specification. Also, FIG. 1 shows by representative arrows 42 and 44 that certain parts of the structure shown in the FIG. 1 may deflect farther out and down (in the case of the parts associated with arrows 42) or farther out and up (in the case of the parts associated with arrows 44) than happens to be shown in FIG. 1. This will also be explained in more detail later in this specification.

Among the components of valve 10 are an annular metal structure 20/30/40, and a leaflet structure 100. Metal structure 20/30/40 forms a complete, continuous annulus around a longitudinal axis (not shown) that passes through the center of the valve. This central longitudinal axis is vertical, given the orientation of the valve shown in FIG. 1. Structure 20/30/40 can be reduced in annular size from the size shown in FIG. 1 by compressing that structure in the annular or circumferential direction. When this is done, structure 20/30/40 shrinks by partial collapse of the diamond-shaped cells 22 and 46 of aortic portion 20 and annulus portion 40. Later FIGS. will show examples of how such cells and/or other collapsible shapes can collapse or shrink in a direction that is annular of the valve. In other words, when the structure is thus made to shrink in the annular direction, the length of the perimeter measured around the outside of the valve becomes smaller. There is no significant change in the overall topological shape of the valve, especially metal structure 20/30/40, between its large and small perimeter sizes or at any time as it transitions between those sizes. For example, if the valve is approximately a circular annulus in its full (FIG. 1) size, it remains an approximately circular annulus as it is reduced to its smaller perimeter size. It is preferred that there be no folding, wrapping, overlapping, or other major topological shape change of metal structure 20/30/40 to reduce its perimeter size or to subsequently re-expand it.

The above-described changes (i.e., collapsing and re-expanding) of metal structure 20/30/40 are preferably all elastic deformations. For example, metal structure 20/30/40 can be resiliently biased to have the size and shape shown in FIG. 1. In such a case, collapsing of metal structure 20/30/40 to the above-mentioned smaller perimeter, annular, or circumferential size can be by elastic deformation of the metal structure, e.g., by confining metal structure 20/30/40 in a tube having a smaller perimeter than the full FIG. 1 size of the valve. Such a tube can be part of apparatus for delivering the valve into a patient. When the valve is pushed or pulled out of the tube, metal structure 20/30/40 automatically, elastically, re-expands to the full size shown in FIG. 1. Because such a delivery tube can be smaller than the full size of the valve, the valve can be delivered into the patient less invasively than would be possible if the valve was only capable of always remaining full size as shown in FIG. 1.

As an alternative or addition to full elastic compression and self-re-expansion, re-expansion may be at least partly assisted by other means. For example, an inflatable balloon on a catheter may be used to assist valve 10 to re-expand to its full size. Such a balloon may be temporarily positioned inside valve 10 to accomplish this. This may be done either because the elastic re-expansion is not quite strong enough to get the valve back to full size when adjacent to surrounding native tissue of the patient, because some plastic re-expansion is required to get the valve back to full size, to help ensure that the valve does in fact firmly seat in and engage the desired surrounding native tissue at the implant site, or for any other reason. For the most part it will be assumed herein that all or substantially all compression and re-expansion are elastic, but the possibility of some plastic compression and re-expansion is also contemplated as mentioned earlier in this paragraph.

We turn now to a description of the various parts of metal structure 20/30/40. Part 20 is intended for implantation in the patient's native aorta downstream from the native aortic valve location, and also downstream from the patient's native valsalva sinus. Part 20 may therefore be referred to as the aortic portion of the valve or of metal support structure 20/30/40. Portion 20 is a completely annular (continuous) structure, with the ability to annularly collapse and re-expand as described earlier in this specification. Portion 20 is made up principally of an annular array of parallelogram- or diamond-shaped cells 22, which give portion 20 the ability to annularly compress and re-expand as described.

Part 40 is intended for implantation in the patient's native aortic valve annulus. Part 40 may therefore be referred to as the annulus portion of the valve or of metal support structure 20/30/40. Part 40 is also a completely annular (continuous) structure, with the ability to annularly collapse and re-expand as described earlier in this specification. Part 40 is again made up primarily of an annular array of parallelogram- or diamond-shaped cells 46, which give portion 40 the ability to annularly compress and re-expand as described.

Part 40 also includes three commissure post members 50 that are spaced from one another (e.g., approximately equally) around the valve. Each commissure post member 50 is intended for implantation at the approximate angular or circumferential location of a respective one of the patient's native aortic valve commissures. Like the native commissures, posts 50 are structures at which adjacent ones of the three leaflets of structure 100 came together in pairs. The blood inflow edge portions (lower as viewed in FIG. 1) of each leaflet are also secured to other structure of the valve below posts 50. The blood outflow edge portions of leaflets 100 (upper as viewed in FIG. 1) are free (except for their end attachments to a respective pair of posts 50). These free edges can come together to close the valve when blood pressure downstream from the valve is greater than blood pressure upstream from the valve. When the blood pressure differential reverses, the greater upstream blood pressure pushes the free edges of the leaflets apart, thereby opening the valve to allow blood flow through it.

Leaflet structure 100 is typically made of three flexible leaflet sheets. The material of these sheets can be any known flexible leaflet material such as appropriately treated natural tissue, a flexible polymer, or the like.

Each of commissure posts 50 is preferably at least partly cantilevered up (in the blood flow direction) from remaining structure of part 40. For example, toward its blood inflow (lower) end, each of posts 50 may be attached to other structure of part 40 only near and/or below the middle of that part in the longitudinal (vertical) direction. At least the upper (blood outflow) end portion of each post 50 is therefore cantilevered from that post's lower-end-portion connections to other structure of part 40. The upper end portion of each post 50 is accordingly preferably a free end (i.e., without any metal connection to other adjacent metal structure of part 40). This has a number of advantages. One of these advantages is that it makes at least the upper portions of posts 50 at least somewhat independent of the other metal structure 20/30/40 of the device. This makes it possible for at least the upper portions of posts 50 to have properties like flexure characteristics, deflection characteristics, final location characteristics, etc., that can be optimized for the purposes that these post portions must serve, while other portions of metal structure 20/30/40 can be relatively independently optimized in these various respects for the various purposes that these other portions of structure 20/30/40 must serve. As an example of this, it may be desirable for the upper portions of posts 50 to stand relatively straight up and to have flexibility that is optimized for absorbing stress from the lateral edges of the leaflets 100 that are attached to those posts. At the same time, it may be desirable for other portions of metal structure 20/30/40 that are at the same general level along the longitudinal axis of the valve to flare radially out to various degrees. This will be described in more detail later in this specification. But just to complete the point that has been started here, it may be desired for the upper portions of cells 46 to be strong enough to hold back native leaflets and/or native leaflet remnants, and/or to deflect down onto the blood outflow surface of the native valve annulus (especially in cases in which the native leaflets have been wholly or largely removed). Similarly, it may be desirable for the members of strut structures 30 to begin to incline radially outwardly as they extend toward circumferentially larger aortic portion 20 and/or as they pass through the patient's native valsalva sinus, which is also circumferentially larger than the native valve annulus.

Clarification of a point of terminology may be appropriate here. When this specification speaks of a structure extending radially outwardly or the like, this does not necessarily mean that this structure is exactly perpendicular to a longitudinal axis extending in the blood flow direction through the valve. It may only mean that the structure has at least some component of alignment that is radial of the valve, i.e., that the structure (or a geometric projection of the structure) forms some angle with the above-mentioned longitudinal axis. In short, as a general matter, a "radially extending structure" or the like does not have to be fully or exactly radial of the above-mentioned longitudinal axis, but may instead have only some vector component that is radial of that axis.

Figure 28:
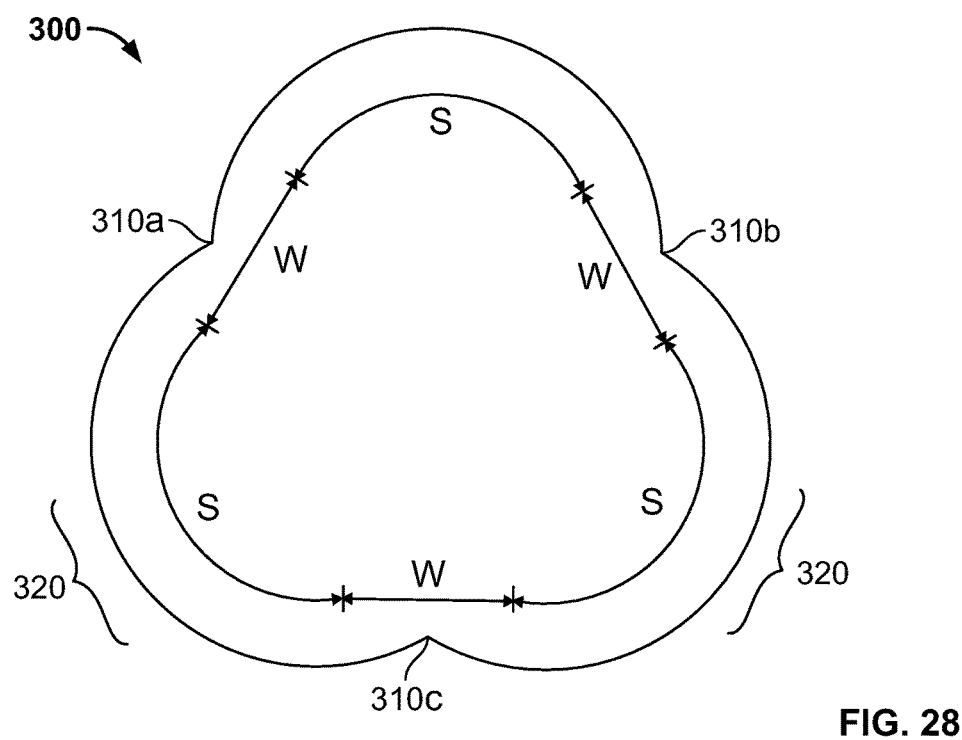
FIG. 28 is a simplified cross section of a typical patient tissue structure that is useful for explaining certain principles of the invention.

The aortic portion 20 and the annulus portion 40 of metal structure 20/30/40 are connected to one another by what may be termed struts or strut structures 30. In the illustrative embodiment shown in FIG. 1 there are six of these struts 30. They are in three pairs, with each pair being adjacent to a respective one of the three commissure posts 50. More particularly, the two struts 30 in each pair are preferably located adjacent (and relatively close to) respective opposite sides of the associated post 50. This arrangement leaves relatively large open areas (in the circumferential direction) between the pairs of struts 30. In other words, the distance in the circumferential direction between the struts 30 in any pair of those struts is preferably less than the circumferential distance between the two circumferentially closest struts in any two different pairs of those struts. Because commissure posts 50 are angularly or rotationally aligned with the patient's native aortic valve commissures, and because struts 30 pass through the patient's native valsalva sinus relatively close to longitudinal projections of posts 50, struts 30 are thus located to pass through the valsalva sinus (typically close to or at the wall of the valsalva sinus) along paths that are circumferentially spaced from the ostia of the patient's coronary arteries. In other words, struts 30 are preferably located in the circumferential direction to pass through the valsalva sinus without any possibility of a strut obstructing the ostium of a coronary artery. (Although patient anatomy can vary in this respect, the coronary artery ostia are typically located in the valsalva sinus between the native aortic valve commissures (or between longitudinal projections of the native aortic valve commissures). See also the later discussion of FIG. 28, which discussion applies to embodiments of the kind generally illustrated by FIG. 1. In particular, in the terms later discussed in connection with FIG. 28, all material of structure 30 at the level of the coronary artery ostia should be confined to areas W as shown in FIG. 28.)

In addition to the characteristics that are mentioned above, each of struts 30 is preferably serpentine in the longitudinal direction (i.e., as one proceeds along the length of any strut 30 from annulus portion 40 to aortic portion 20, the strut deviates from a straight line, first to one side of the straight line, then to the other side of the straight line, then back to the first side, and so on). One of the benefits of this type of strut configuration is that it can increase the lateral flexibility of structure 20/30/40, especially the lateral flexibility of strut portion 30 between portions 20 and 40. Lateral flexibility means flexibility transverse to a longitudinal axis that is parallel to blood flow through the valve. Prior to and during implantation, this lateral flexibility can help the valve more easily follow curves in instrumentation that is used to deliver the valve into the patient. After implantation, this lateral flexibility can help each of portions 20 and 40 seat more concentrically in its respective portion of the patient's anatomy, which portions may not be exactly perpendicularly concentric with one single, common, central longitudinal axis.

As shown in FIG. 1, the upper end of each strut 30 may connect to the lower end (or apex) of one of the cells 22 of aortic portion 20. The lower end of each struts 30 may similarly connect to the upper end (or apex) of one of the cells 46 of annulus portion 40. It should be noted, however, that especially at the lower end of strut structure 30 there are other cells 46 of annulus portion 40 that have no struts 30 connected to their upper ends or apexes. For example, arrows 42 are shown adjacent to the upper ends of two representative ones of cells 46 of this kind. These are the cells 46 whose upper portions can be configured to deflect or project radially outwardly (as indicated by the arrows 42) for such purposes (mentioned earlier, and also in more detail later) as holding back any remaining native leaflet material and/or clamping down on the blood outflow side of the patient's native valve annulus.

From the foregoing, it will be seen that the features of valve 10 for holding the valve in place in the patient can include any or all of the following: (1) the radially outward projection of some or all of the lower portions of annulus cells 46 adjacent the blood inflow side of the native aortic valve annulus; (2) the radially outward projection of the upper portions of at least some of the upper portions of annulus cells 46 adjacent possibly remaining native aortic leaflet tissue and/or adjacent the blood outflow side of the native aortic valve annulus; (3) the general radial outward expansion of annulus portion 40 against the native valve annulus; (4) the radial outward expansion of aortic portion 20 to annularly engage the inner wall surface of the aorta downstream from the valsalva sinus; and (5) the possible engagement of the inner wall surface of the valsalva sinus by strut structures 30 passing through that sinus. Although not shown in FIG. 1, it is possible to add to any suitable portion(s) of metal structure 20/30/40 barbs that project out from other adjacent structure so that they additionally engage, dig into, and/or penetrate tissue to give the implanted valve additional means for maintaining its position in the patient.

Note also that in addition to possibly engaging possibly remaining native aortic valve leaflet tissue, valve 10 has many structures for pushing any such remaining tissue radially outwardly away from possible interference with prosthetic leaflet structure 100. These structures include the upper portions of all of cells 46 and the lower portions of all of struts 30.

There are some other possible features of valve 10 that have not yet been mentioned. One of these aspects is the provision of apertures like 52 through commissure posts 50 (and possibly other portions of metal structure 20/30/40) for facilitating the attachment (e.g., using suture material or other similar strand material) of leaflet structure 100 to the metal structure. Other layers of material such as tissue, fabric, or the like may also be attached to various parts of metal structure 20/30/40 for various purposes. These purposes may include (1) helping to prevent, reduce, or cushion contact between leaflet structure 100 and metal structure 20/30/40; (2) helping to improve sealing between the valve and the surrounding native tissue (e.g., to prevent paravalvular leakage); and (3) helping to promote tissue in-growth into the implanted valve. Limited examples of such additional layers of material are shown in FIG. 1 in the form of lower fabric skirt 110 and blood inflow edge sealing ring 120. Both of structures 110 and 120 extend annularly around the outside of the lower (blood inflow) edge of valve 10. Structures like 110 and 120 may be held to metal structure 20/30/40 by sutures or other similar strand-like material, and apertures (like 52) through the metal structure (or other features of the metal structure) may be used to provide anchoring sites for such sutures or the like. Still other possible aspects of valve 10 will be discussed in connection with later FIGS.

A possibly important feature of valves in accordance with the present invention is that they can include a structure near the blood inflow edge for clamping adjacent native tissues in a particular way. In particular, the upper and lower portions of at least some of cells 46 can both pivot toward one another from a common central location. This is illustrated schematically in FIGS. 2 and 3.

Figure 2:
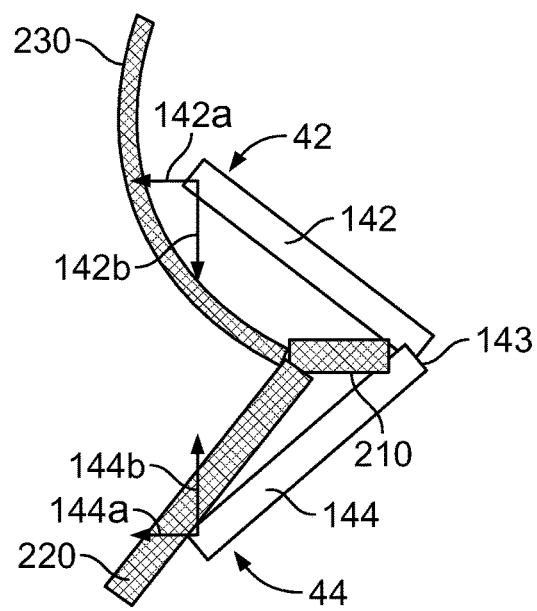
FIG. 2 is a simplified schematic diagram of a representative portion of apparatus like that shown in FIG. 1 in relation to some native tissue structures of a patient in accordance with the invention.

FIG. 2 shows the somewhat simpler case in which the patient's native aortic valve leaflets have been removed prior to implanting valve 10. The native tissue structures that are visible in FIG. 2 are a portion 220 of the wall of the left ventricle, a portion 210 of the aortic valve annulus, and a portion 230 of the wall of the valsalva sinus. The upper portion of a representative cell 46 from FIG. 1 is shown schematically in FIG. 2 by member 142. The lower portion of that cell is shown schematically by member 144. Members 142 and 144 can pivot toward one another about central pivot point 143. As in FIG. 1, this is again indicated by arcing arrows 42 and 44. Thus members 142 and 144 initially form a relative large, open jaw structure, the two jaws of which can be released to resiliently pivot toward one another to clamp down on any tissue within their reach. In the case of FIG. 2, this can include some of the tissue of sinus wall 230 and the upper surface of annulus 210 (for upper pivoting member 142), and some of the tissue of left ventricle wall 220 and the lower surface of annulus 210 (for lower pivoting jaw member 144). Clamping force vector component diagrams in FIG. 2 indicate the nature of the clamping forces that can result from these kinds of tissue engagement. For example, member 142 can have a radially outward clamping force component 142a and a longitudinally downward clamping force component 142b. Similarly, member 144 can have a radially outward clamping force component 144a and a longitudinally upward clamping force component 144b. Opposing clamping force components 142b and 144b tend to clamp tissue between members 142 and 144. But radially outward force components 142a and 142b also engage tissue and therefore also help to hold valve 10 in place in the patient.

Figure 3:
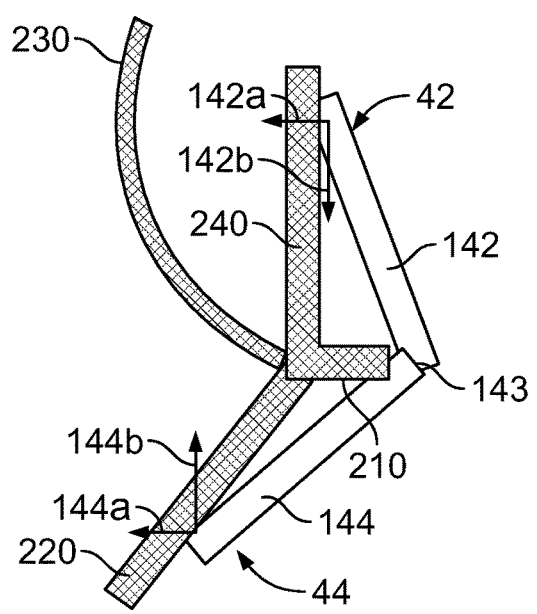
FIG. 3 is generally similar to FIG. 2 for some other native tissue structures of a patient.

FIG. 3 illustrates the somewhat more elaborate case in which native aortic leaflet tissue 240 (typically, or at least often, stenotic) remains in the vicinity of prosthetic valve 10 when the valve is implanted. FIG. 3 shows that in this type of situation upper member 142 both engages leaflet tissue 240 and helps to push it radially out of the way. Again, member 142 exerts both a radially outward force component 142a and a longitudinal (downward) force component 142b on the adjacent tissue (in this case leaflet tissue 240). The behavior and effects of lower member 144 are similar to what is shown in FIG. 2 and described earlier. Thus again the structures of valve 10 exert both radial outward tissue engaging forces 142a/144a and oppositely directed tissue clamping forces 142b/144b to hold valve 10 in place in the patient.

Recapitulating and extending the above, the attachment method of the present design applies forces in the radial and longitudinal directions to clamp onto several anatomical features, not just annulus 210. In doing this, a valve in accordance with this invention can maximize (or at least significantly increase) the orifice area at the annulus level for better blood flow. Another way of thinking about the present designs is not necessarily as "clamps," but rather as members of a stent 40 that conform to the different diameters of different portions of the anatomy. Structures that only "clamp" tend to engage only both sides of the native annulus (like 210), and do not also extend to and engage other tissue structures as in the present designs. The present structures also differ from "clamp" structures that terminate from a single pointed wire. Instead, in the present designs, the conforming members are formed from continuous strut members of the base (annular portion 40) of the stent. This can only be achieved with an annulus portion 40 that stays below the ostia of the coronary arteries and with commissure posts 50 that are "independent" of other structure of annulus portion 40 as was described earlier in this specification.

Still other features of the present valves that warrant emphasis are mentioned in the following. The annulus portion 40 of the present valves preferably expands as nearly as possible to the full size of the native valve annulus. The leaflet structure 100 is preferably mounted just inside annulus portion 40. This helps the present valves avoid any stenotic character (such as would result from having the leaflet structure or some other structure on which the leaflet structure is mounted) spaced radially inwardly from annulus portion 40. The present valves are thus ensured to have the largest opening for blood to flow through, which reduces the pressure gradient (drop) across the valve.

Note that at the level of the coronary artery ostia, the present valves have only very minimal non-leaflet structure 30; and even that minimal non-leaflet structure is rotationally positioned to pass through the valsalva sinus where it will safely bypass the coronary artery ostia. Annulus portion 40 is preferably designed to be entirely upstream (in the blood flow direction) from the coronary artery ostia. Aortic portion 20, on the other hand, is preferably designed to be entirely downstream from the coronary artery ostia (i.e., in the aorta downstream from the valsalva sinus). Some prior designs have much more extensive non-leaflet structures extending much farther into or through the valsalva sinus and therefore longitudinally beyond the coronary artery ostia. This is believed to be less desirable than the present structures.

The present valves preferably include "independent" commissure posts 50 that are "lined up" or aligned with (i.e., superimposed over) the native valve commissures. This also helps to ensure proper coronary artery flow, when combined with the fact that struts 30 are confined to being closely adjacent to posts 50 in the circumferential direction. Even relatively thin connecting members (like struts 30) could partially block a coronary artery if not correctly positioned in the circumferential direction around the valsalva sinus. But this is avoided in the present valves by the principles and features mentioned, for example, in the immediately preceding sentences.

Figure 4:
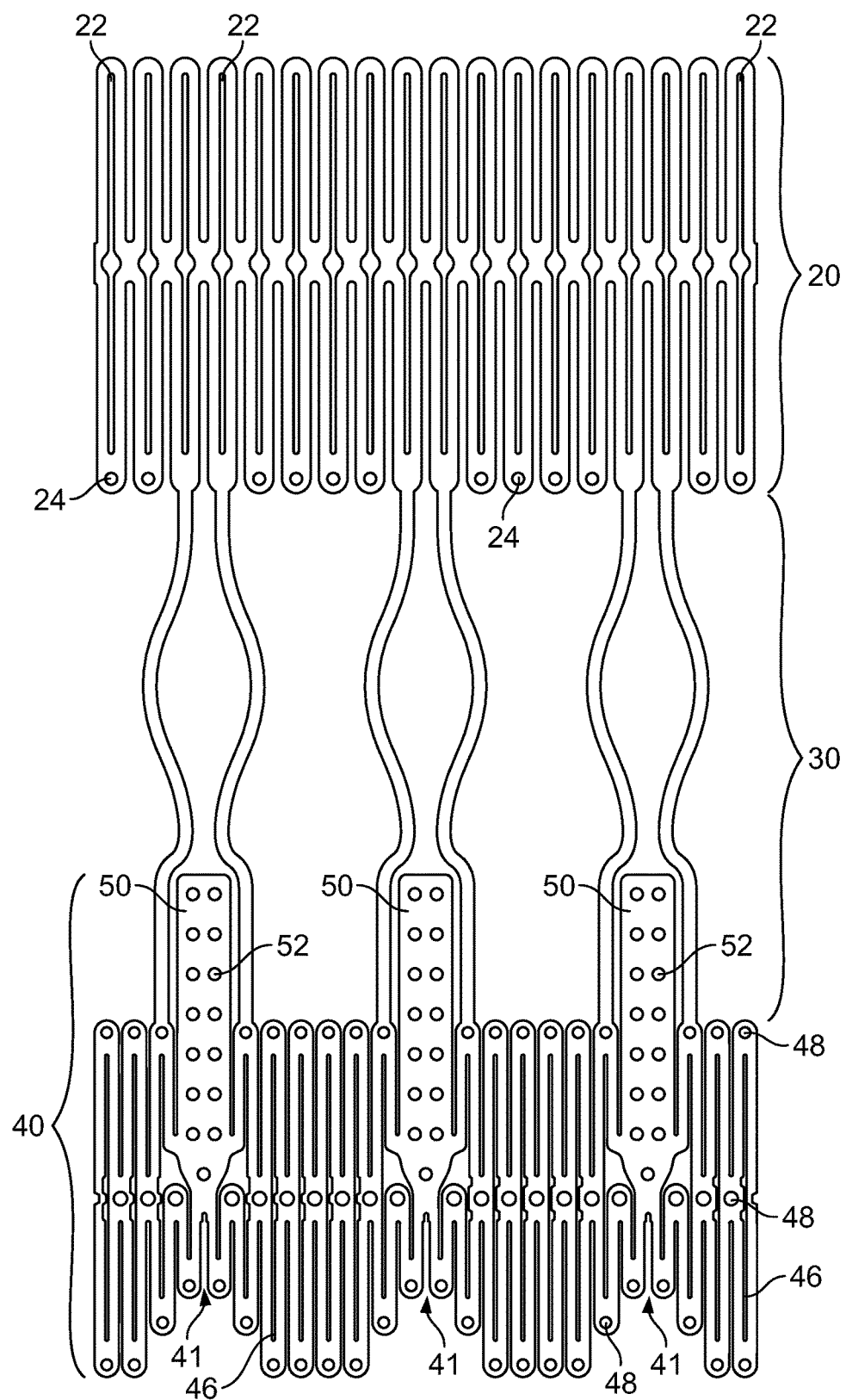
FIG. 4 is a simplified elevational view of another illustrative embodiment of apparatus in accordance with the invention.

FIG. 4 shows another illustrative embodiment of metal support structure 20/30/40. FIG. 4 shows this structure as though cut along its length and then laid flat. FIG. 4 also shows this structure in the condition that it has in its circumferentially collapsed condition. Thus, for example, the sides of what will be diamond-shaped cells 22 and 46 in the re-expanded valve are, in FIG. 4, collapsed down to being parallel with one another. Again, the fact that FIGS. like FIG. 4 show structures as though cut longitudinally and laid flat is only for ease and convenience of depiction. In actual fact these structures are complete and continuous annular structures like the structure 20/30/40 shown in FIG. 1.

Note that in the FIG. 4 design there are eyelets 24 in aortic section 20 for attachment of material and/or attachment of wires/sutures for a delivery system. On annulus section 40 the eyelets 48/52 can be used for attachment of the cuff, porcine buffer, and/or leaflets. FIG. 4 shows an annulus portion 40 with a "scalloped" inflow (lower) edge. This scalloped blood inflow edge is relatively "high" in the vicinity of the inflow end of each commissure post 50, and relatively "low" between commissure post 50 inflow ends. ("High" means more downstream; "low" means more upstream.) This can help the implanted valve avoid affecting the patient's mitral valve, which tends to be radially spaced from the aortic valve along a radius of the aortic valve that corresponds to the radial location of one of the aortic valve's commissures. Because the valves of this invention are preferably implanted with posts 50 superimposed inside the native valve commissures, this places one of the "high"

portions 41 of the inflow edge adjacent the patient's mitral valve. The resulting recessing 41 of annulus portion 40 helps the prosthetic valve avoid interfering with the mitral valve.

Figure 5:
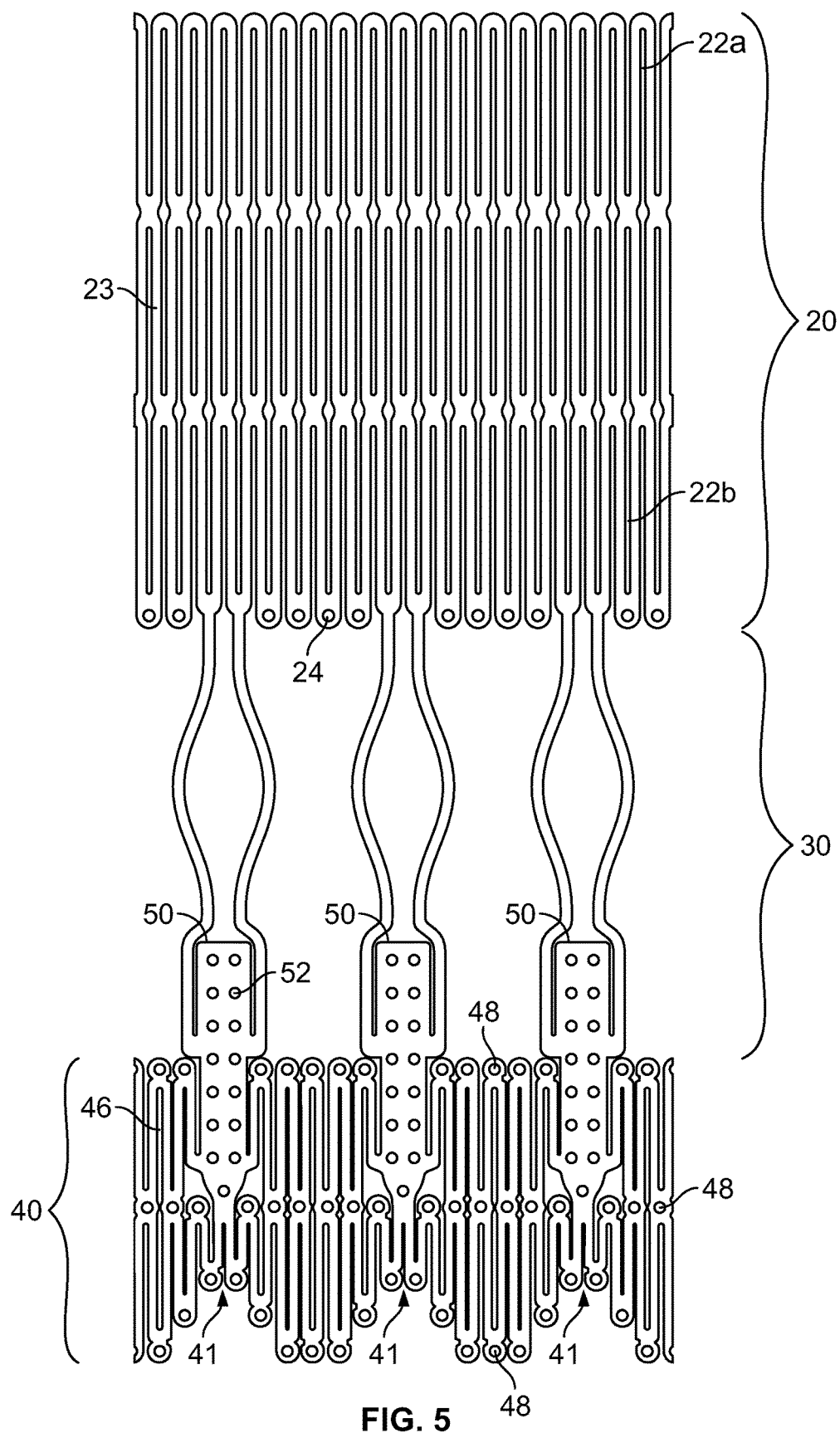
FIG. 5 is generally similar to FIG. 4 for another illustrative embodiment in accordance with the invention.

FIG. 5 shows yet another illustrative embodiment of metal support structure 20/30/40. FIG. 5 shows this embodiment in the same general way and condition as FIG. 4 shows its embodiment. Thus, as said in connection with FIG. 4, the structure shown in FIG. 5 is actually a complete, continuous annulus, and the longitudinally cut and flattened depiction shown in FIG. 5 is only employed for simplicity and greater clarity.

The FIG. 5 embodiment again has eyelets 24 in the aortic section 20 for attachment of material and/or attachment of wires/sutures for a delivery system. Also, eyelets 48/52 on annulus section 40 can be used for attachment of the cuff, porcine buffer, and/or leaflets. As compared to the FIG. 4 design (in which connecting support struts 30 are connected to the downstream apexes of certain annulus portion cells 46), in FIG. 5 the connecting support struts 30 are connected directly to posts 50. The aortic portion 20 of the FIG. 5 embodiment also has two annular arrays of cells 22a and 22b (rather than only one annular array of such cells 22 as in the earlier embodiments). Array 22a is more downstream than array 22b, but these two arrays do overlap somewhat in the longitudinal direction by virtue of the cells in the two arrays having some intervening cell members (like representative member 23) in common.

A typical way of making any of the support structures 20/30/40 of this invention is to laser-cut them from a tube.

Figure 6:
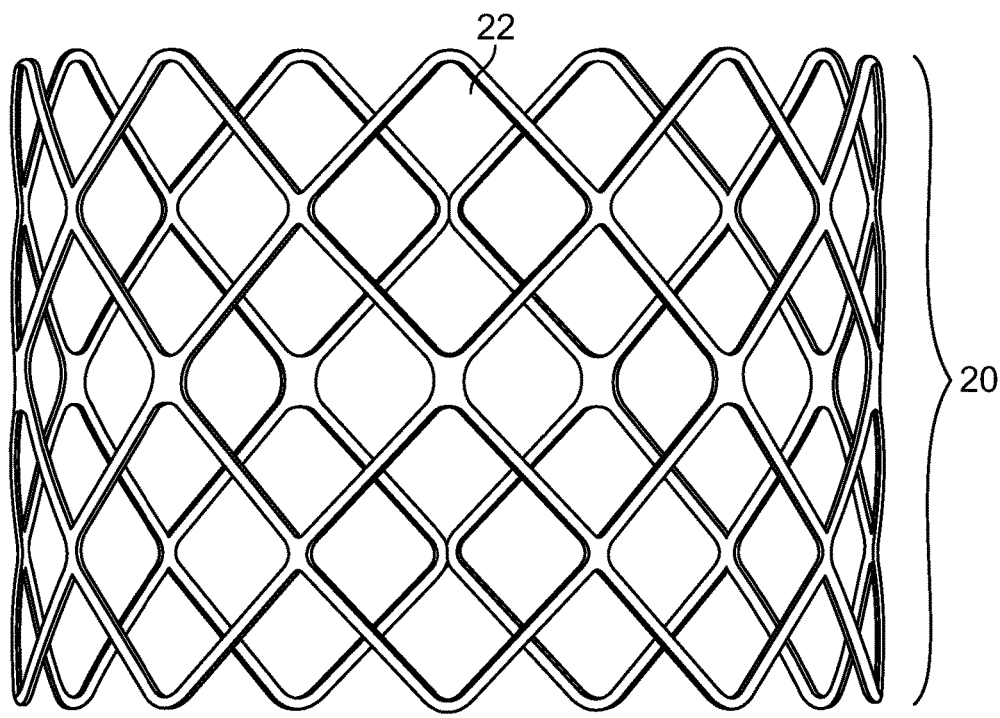
FIG. 6 is a simplified elevational view of another illustrative embodiment of apparatus in accordance with the invention.

FIG. 6 shows another illustrative embodiment of aortic portion 20, in which the cells 22 of the mesh stent can expand against the ascending aorta. This structure may or may not be covered in tissue, polymer, and/or fabric (true for any of the embodiments shown and described herein).

Figure 7:
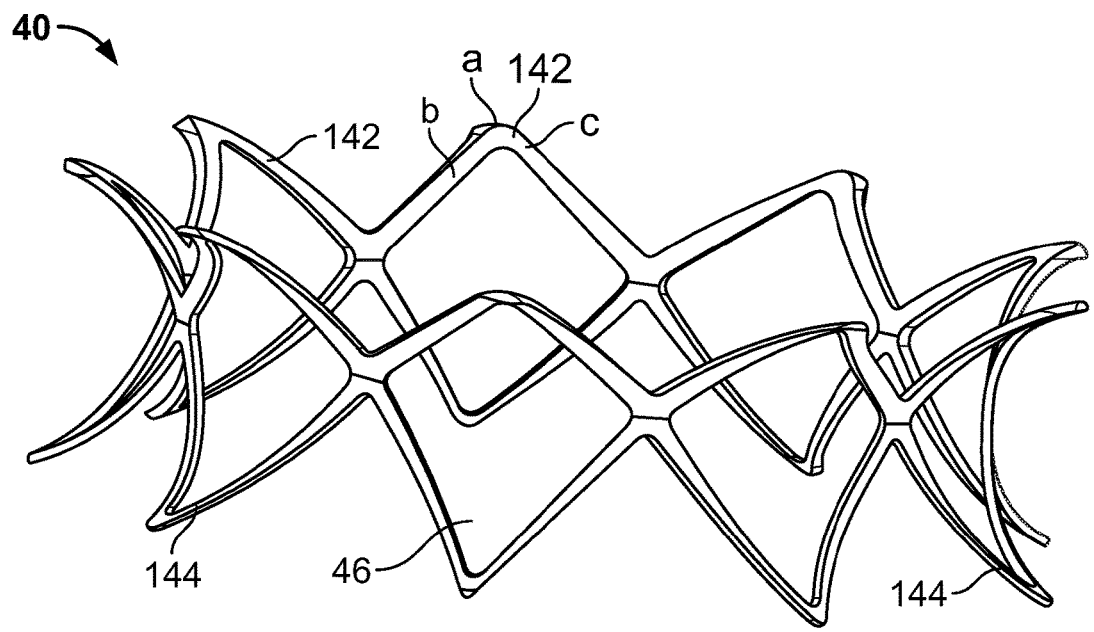
FIG. 7 is a simplified perspective view of another illustrative embodiment of apparatus in accordance with the invention.
Figure 8:
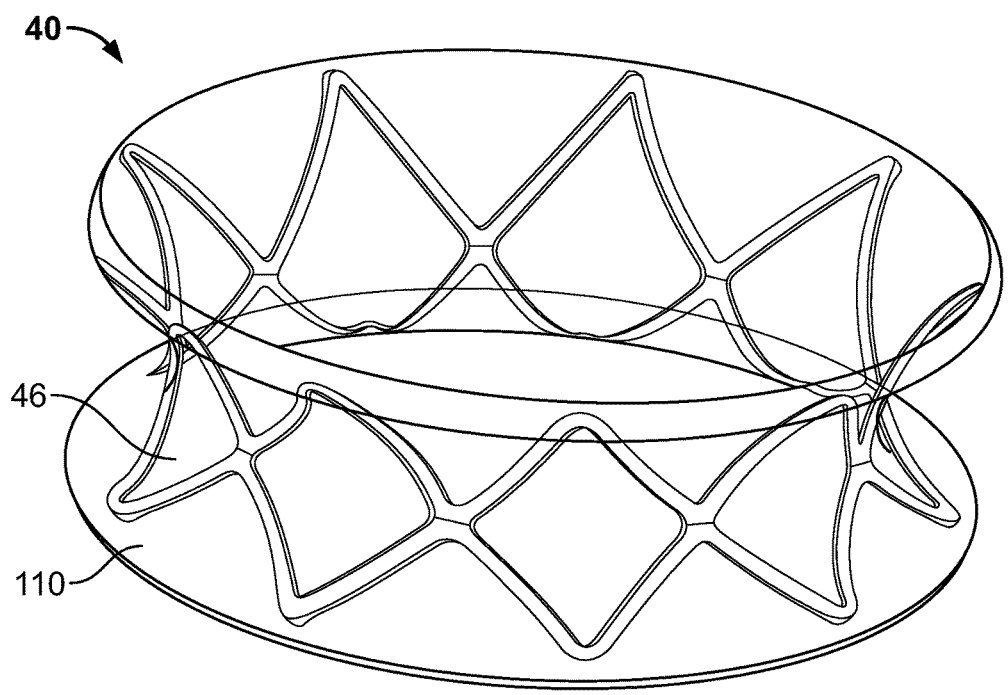
FIG. 8 is a simplified perspective view showing an illustrative embodiment of another component added to what is shown in FIG. 7 in accordance with the invention.

FIGS. 7 and 8 show another illustrative embodiment of annulus portion 40. This mesh stent has expandable cells that press against the native valve annulus and/or leaflets (if the native leaflets remain). Upper 142 and lower 144 portions of this stent clamp down on the native annulus and/or leaflets. This stent design is symmetrical around the circumference, but it may be asymmetrical to allow anatomical conformance with the mitral valve, for example. A cuff 110 made of fabric, tissue, or polymer may fully or partially encapsulate this stent as shown, for example in FIG. 8.

Figure 9:
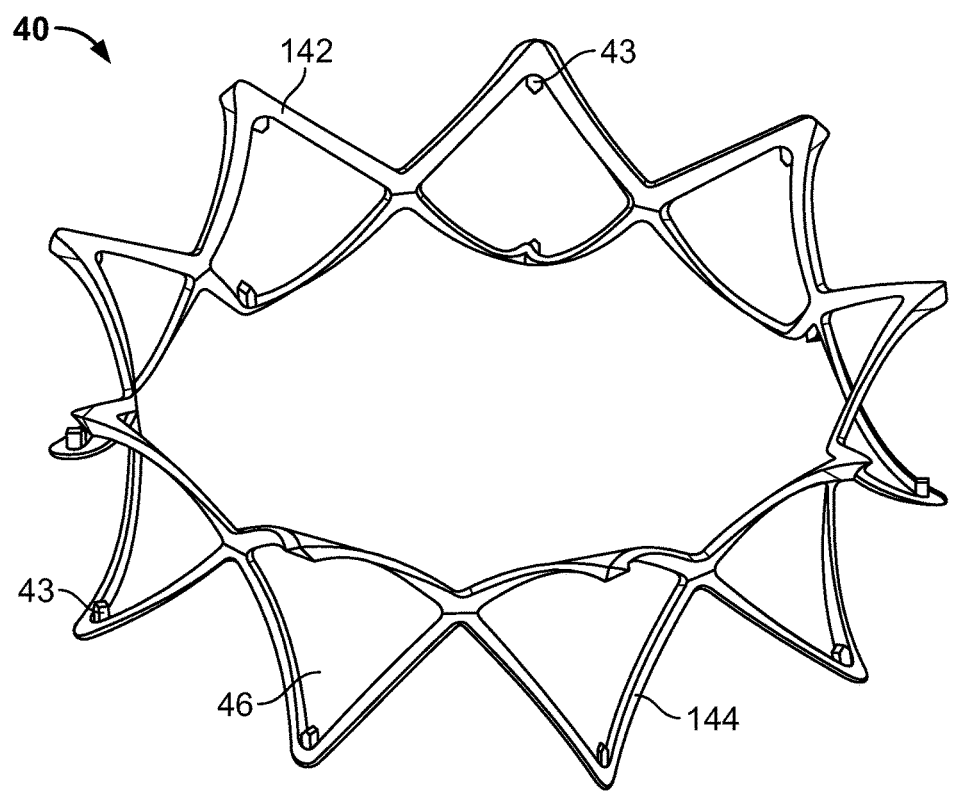
FIG. 9 is generally similar to FIG. 8, but shows an alternative embodiment with additional possible features in accordance with the invention.
Figure 10:
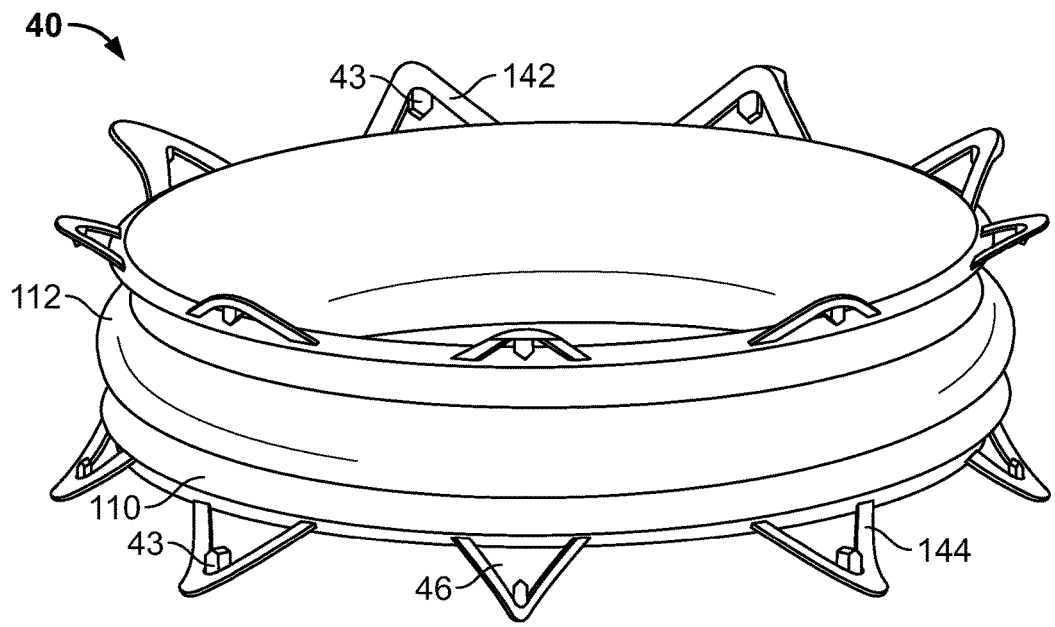
FIG. 10 is generally similar to FIG. 9, but shows an illustrative embodiment of more components added to what is shown in FIG. 9 in accordance with the invention.

FIGS. 9 and 10 show an embodiment of stent 40 that includes a set of barbs 43 on the top and/or bottom to further secure the stent in order to stop migration. A partial cuff 110 (FIG. 10) allows the barbed tips 43 to be exposed to direct tissue contact for enhanced securing. The bottom section could be asymmetrical (e.g., as in FIGS. 4 and 5) to mitigate any impingement on the mitral valve. An extra-thick, toroidal section 112 of the cuff allows extra sealing capacity to prevent paravalvular leakage.

Figure 11:
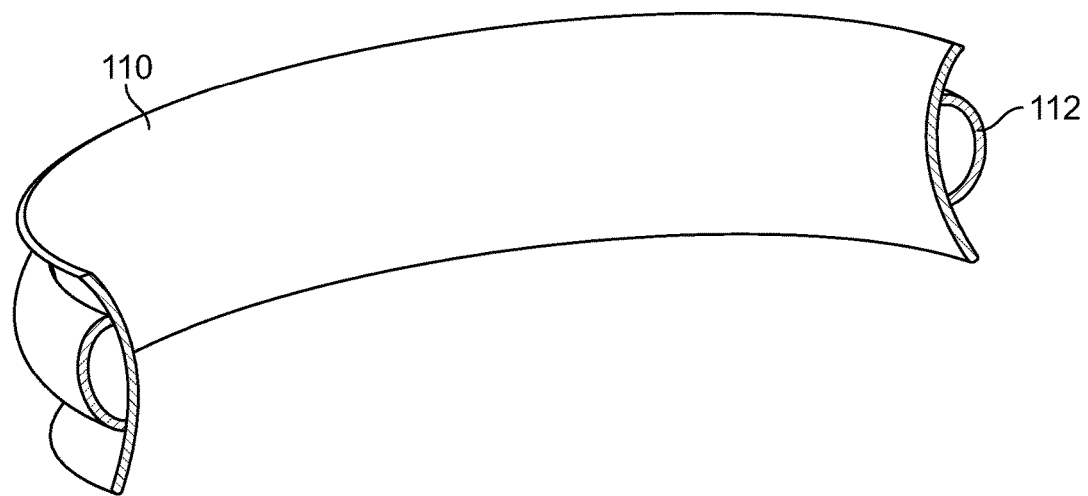
FIG. 11 is a simplified perspective view showing in more detail a representative portion of the components that are added in FIG. 10.

FIG. 11 shows that toroidal section 112 of cuff 110 allows extra sealing capacity to prevent paravalvular leakage. This section could be made of extra fabric, tissue, or polymer. The chamber 114 inside section 112 can accommodate an injectable polymeric substance to aid in sealing.

Figure 12:
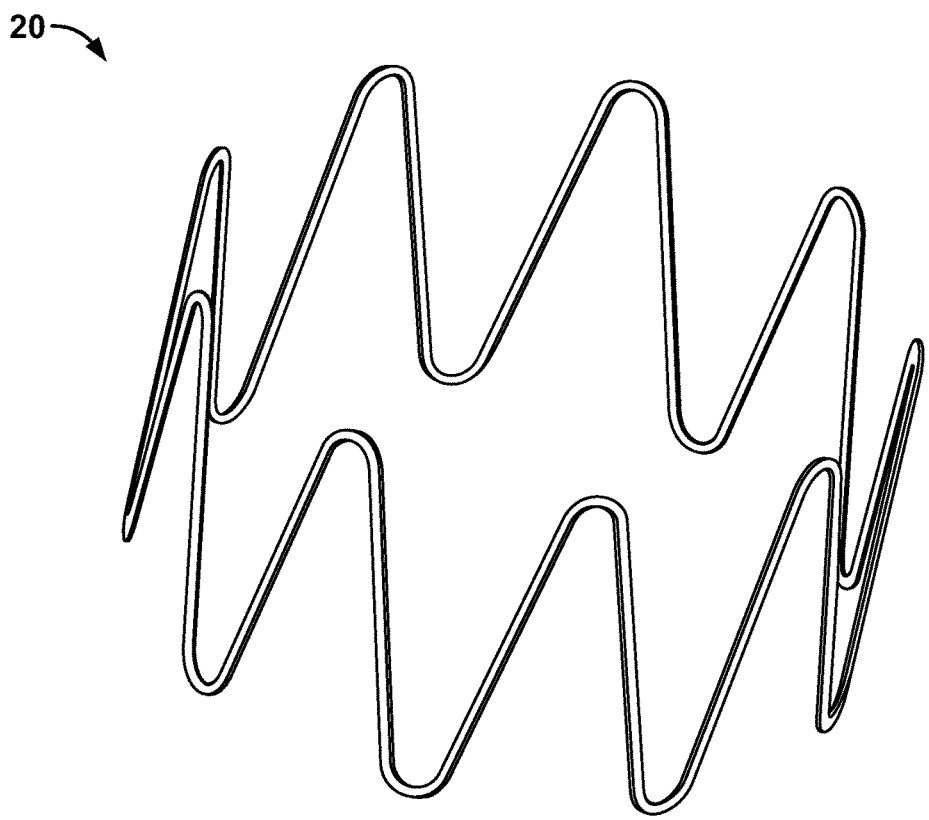
FIG. 12 is a simplified perspective view of another illustrative embodiment of apparatus in accordance with the invention.

FIG. 12 shows another illustrative embodiment of the aortic holding portion 20. In this case portion 20 is a metallic or polymeric expandable wire form with many of the same attributes discussed with the mesh stent.

Figure 13:
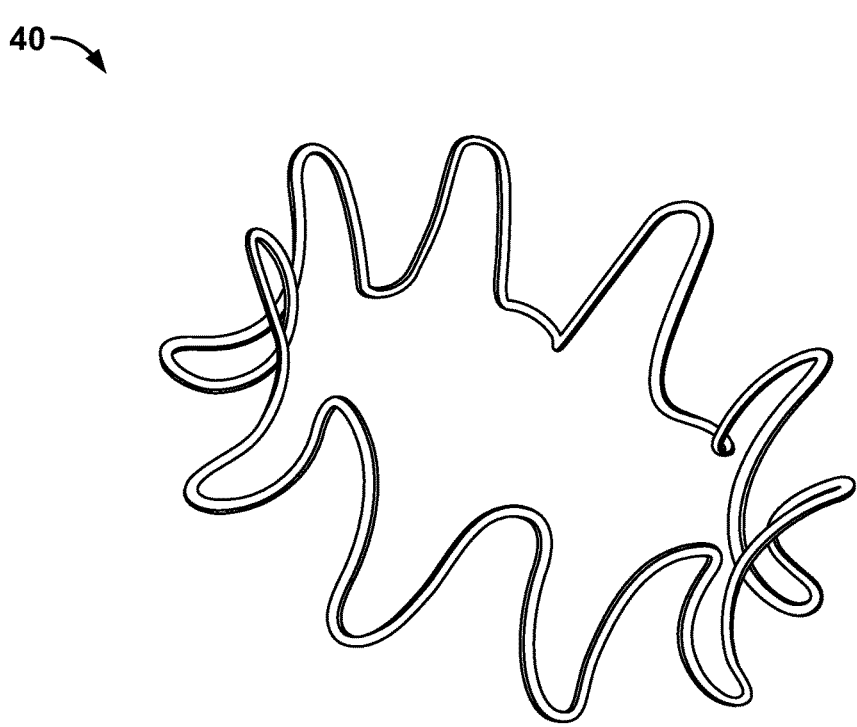
FIG. 13 is a simplified perspective view of another illustrative embodiment of apparatus in accordance with the invention.

FIG. 13 shows another illustrative embodiment of annulus/leaflet holding portion 40. In this case portion 40 is a metallic or polymeric expandable wire form with many of the same attributes discussed with the mesh stent.

Figure 14:
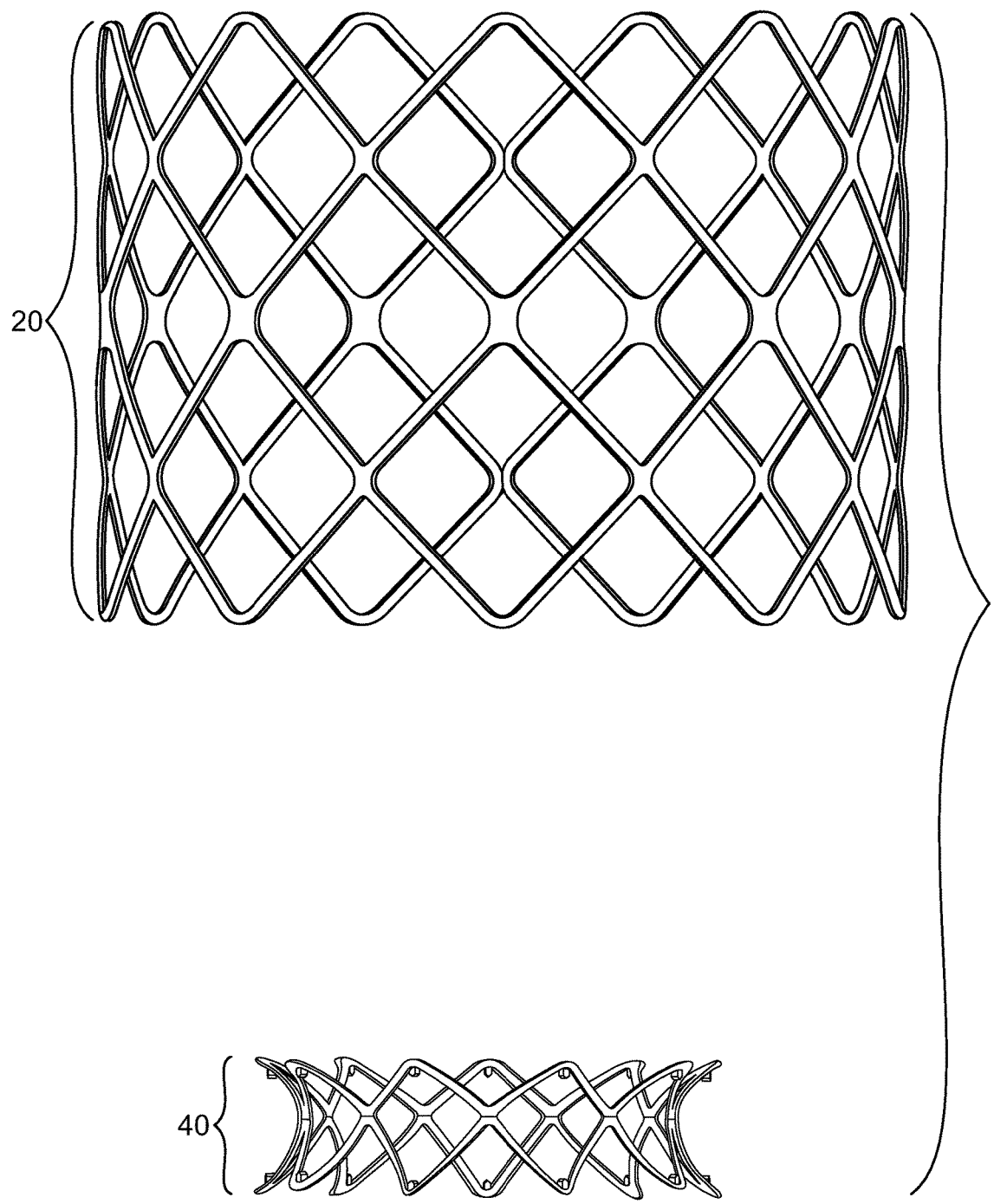
FIG. 14 is a simplified elevational view of still another illustrative embodiment of apparatus in accordance with the invention.
Figure 15:
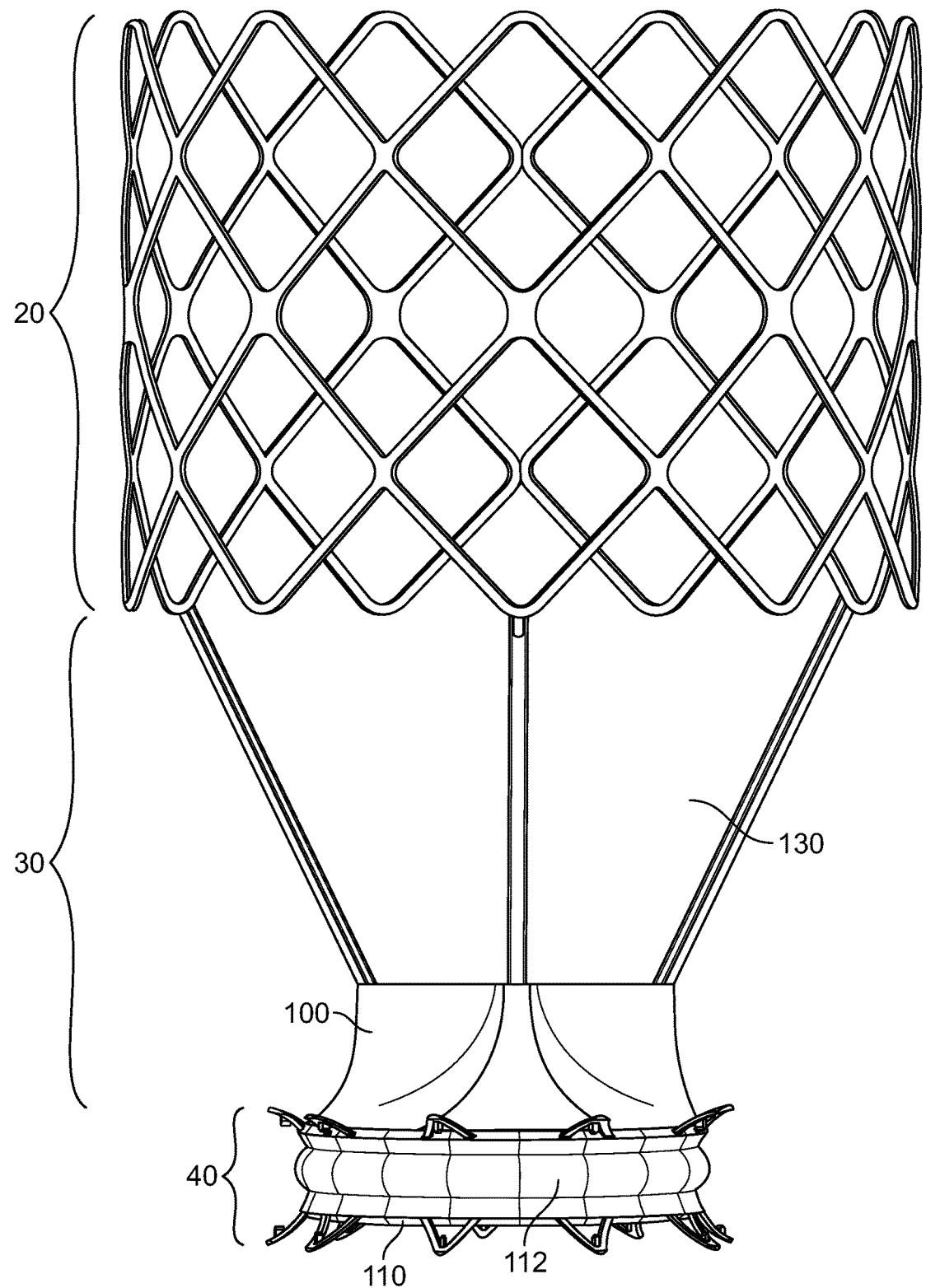
FIG. 15 is generally similar to FIG. 14, but shows an illustrative embodiment of more components added to what is shown in FIG. 14 in accordance with the invention.

FIGS. 14 and 15 show an illustrative assembly of an aortic portion 20 and an annulus portion 40. In FIG. 15 a pliable or semi-rigid reinforced fabric 30 connects the aortic portion 20 and the annulus/cuff portion 40/110/112 to allow somewhat independent movement. The tissue or synthetic leaflets 100 can then be attached to connecting section 30. All of the disclosed variations allow for ample areas (like 130) for blood to flow to the coronaries.

Figure 16:
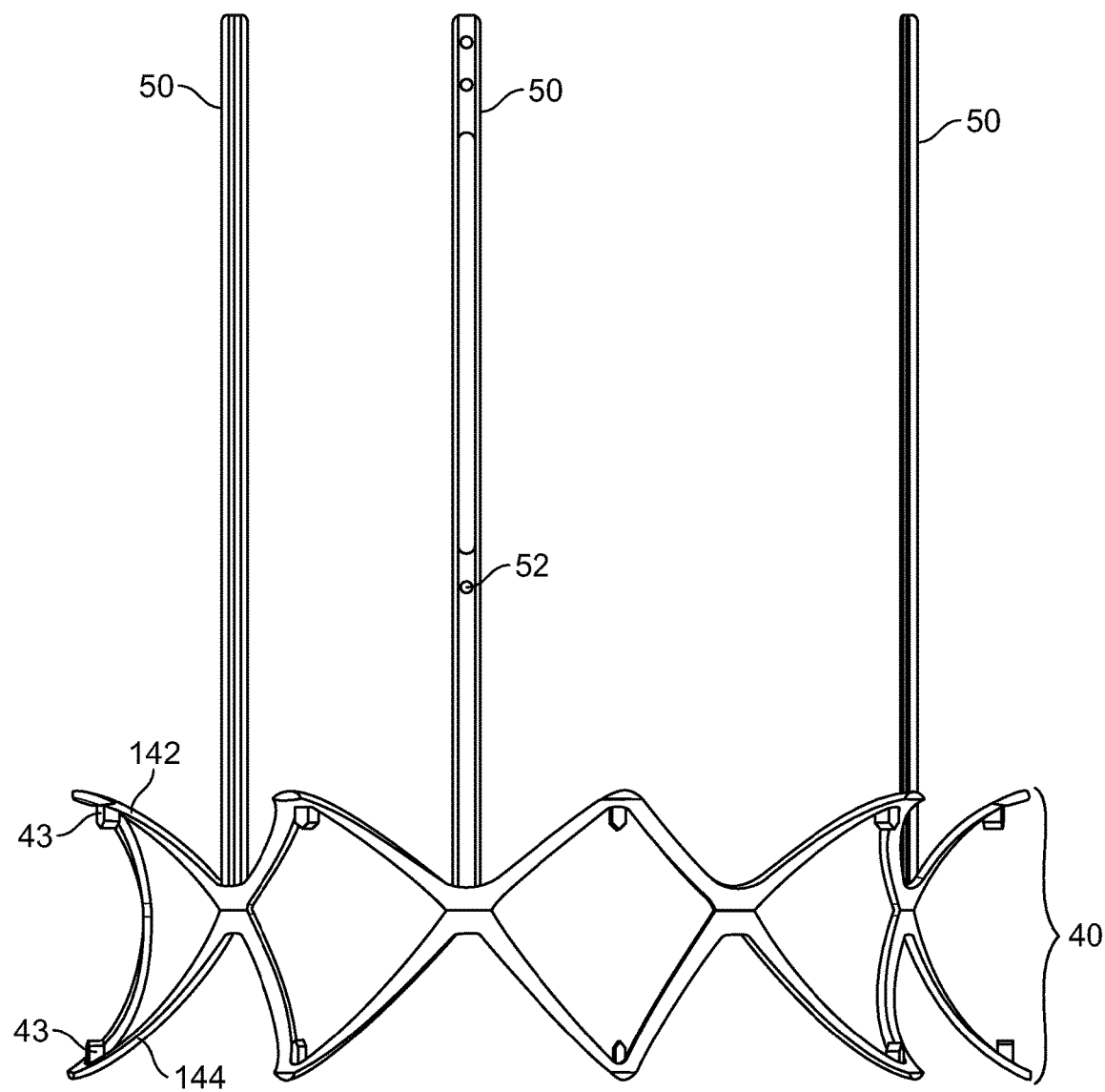
FIG. 16 is a simplified elevational view of another illustrative embodiment of apparatus in accordance with the invention.

The variation shown in FIG. 16 does not include an aortic portion 20. Instead, three independent commissure posts 50 allow for leaflet attachment (e.g., with the aid of apertures 52), while the base 40 is secured in place as described earlier. Posts 50 can be lined up with the native commissures and (by virtue of the recesses like the one identified by reference number 41) allow for an opening on the lower portion to be clear of chordae and the mitral valve. The posts 50 used to attach the leaflets may be solid or have any combination of holes, slots, and/or other apertures 52.

Note that even for an embodiment like FIG. 16, when used for an aortic valve, any non-leaflet portion of the valve (such as commissure posts 50) that extends into the coronary sinus to the level of any coronary artery ostium is confined, in the circumferential direction, to locations that are well spaced from the coronary artery ostia. This is preferably accomplished by having all such non-leaflet structure confined (in the circumferential direction) to locations or areas that are at or circumferentially near the native aortic valve commissures (or downstream projections of those commissures). The circumferential width of each of these areas in which non-leaflet structure is permitted at the level of the coronary artery ostia is preferably less than the circumferential spacing at that level between circumferentially adjacent ones of those areas. It is not a problem for moving leaflet material to extend to or even beyond the level of the coronary artery ostia because the coronary arteries can fill with blood when the valve is closed. But no non-leaflet and therefore basically non-moving part of the prosthetic valve should be allowed to occupy any location at the level of the coronary artery ostia where that non-leaflet material may interfere with blood flow into the coronary arteries.

FIG. 28 illustrates the point made in the immediately preceding paragraph (and also elsewhere in this specification). FIG. 28 shows a cross section of a typical patient's valsalva sinus 300 at the level of the coronary artery ostia. The patient's native aortic commissures (or downstream projections of those commissures) are at locations 310a-c. The coronary artery ostia typically occur in bracketed areas 320. Any non-leaflet structure of a prosthetic valve in accordance with this invention that is at the level depicted by FIG. 28 should be confined to areas W. The width of each of these areas in the circumferential direction (i.e., the dimension W) is preferably less than the distance S in the circumferential direction between any two circumferentially adjacent ones of these areas.

Figure 17:
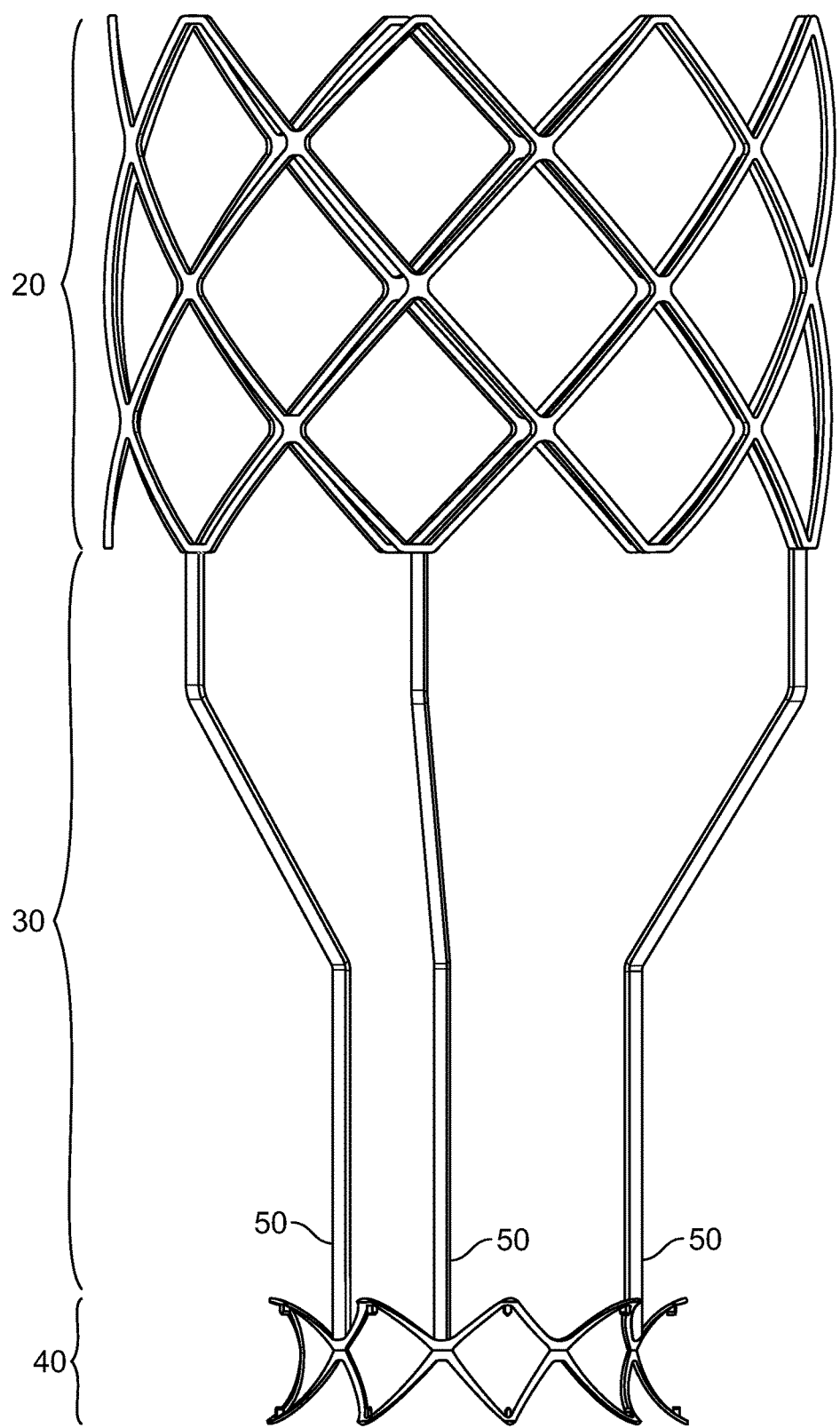
FIG. 17 is a simplified elevational view of another illustrative embodiment of apparatus in accordance with the invention.

FIG. 17 shows another illustrative embodiment that is somewhat like the embodiments in FIGS. 1, 4, and 5 in that there is a continuous link 30 between aortic section 20 and annulus section 40. In this embodiment link structure 30 itself allows for leaflet attachment, with the lower portion of each link 30 acting like a commissure post 50. To mitigate leaflet abrasion at the attachment site in this or any other embodiment, the stent may first be covered with fabric, followed by a thin layer of buffering tissue/polymer, and finally the leaflet tissue/polymer. The stent of the valve can be partially or completely covered in one or a combination of materials (polyester, tissue, etc.) to allow for better in-growth, abrasion protection, sealing, and protection from metal leachables like nickel from nitinol.

Most of the detailed discussion thus far in this specification has related to prosthetic aortic valves. However, certain aspects of what has already been said can also be applied to making prosthetic valves for other locations in the heart. The mitral valve is another valve that frequently needs replacement, and so this discussion will now turn to possible constructions for other valves such as the mitral valve.

In the case of the mitral valve (which supplies blood from the left atrium to the left ventricle), only the native valve annulus area (possibly including what is left of the native valve leaflets) is available for anchoring the prosthetic valve in place. There is nothing comparable to the aorta for additional downstream anchoring of a prosthetic mitral valve.

Structures of the types shown in FIGS. 7-11 and 13 are suitable for use in prosthetic mitral valves. In such use, annular structure 40 may be delivered into the native mitral valve annulus in a circumferentially collapsed condition and then re-expanded to the depicted size and condition in that annulus. The apex portions 142 of cells 46 at one end of structure 40 (e.g., the blood inflow end) project resiliently out and also pivot somewhat downstream as shown, for example, in FIG. 7 and engage the patient's tissue adjacent the inflow side of the patient's native mitral valve annulus. Apex portions 144 of cells 46 at the other end of structure 40 (e.g., the blood outflow end) project resiliently out and also pivot somewhat upstream and engage the patient's tissue adjacent the outflow side of the patient's native valve annulus. The tissue of and adjacent to the mitral valve annulus is thereby clamped between tissue clamping structures 142 and 144. Barbs 43 may be added as shown in FIGS. 9 and 10 for additional tissue engagement and possible penetration to additionally help hold the valve in place in the mitral valve annulus. Other features (e.g., 110 and 120) and principles discussed earlier in connection with FIGS. 7-11 and 13 apply to the possible mitral valve use of these structures and features.

Figure 18:
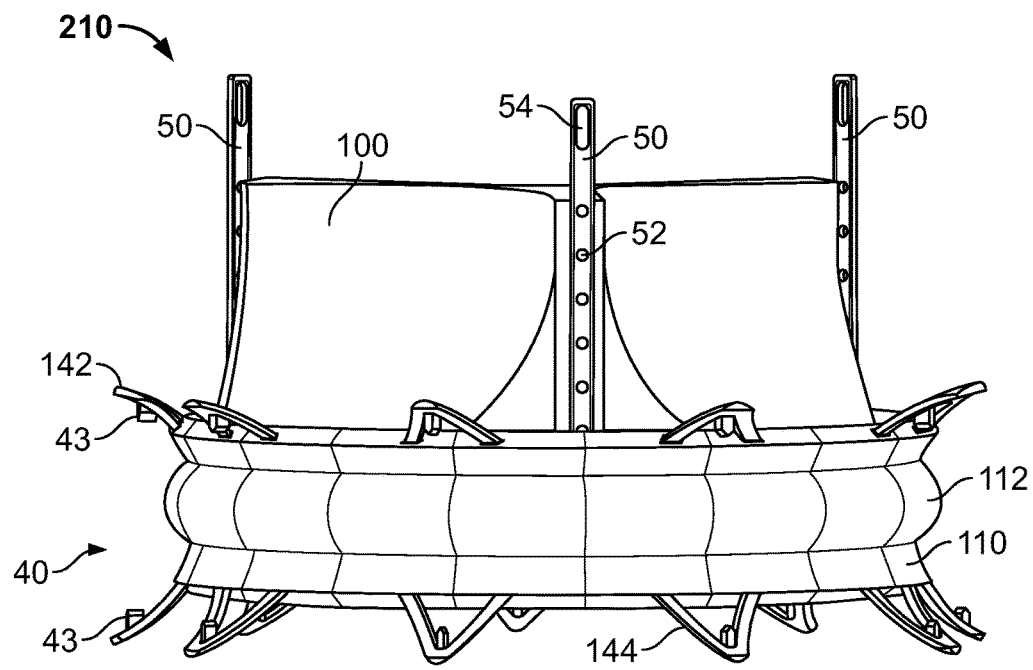
FIG. 18 is a simplified elevational view of another illustrative embodiment of a prosthetic heart valve in accordance with the invention.

An illustrative embodiment of a more fully developed prosthetic mitral valve 210 in accordance with the invention is shown in FIG. 18. In this depiction of mitral valve 210, its blood inflow end is down, and its blood outflow end is up. (This depiction may be regarded as "upside down" as compared to its orientation in a patient who is standing upright.) Analogous to what is shown in FIG. 16, valve 210 has three commissure posts 50 that are cantilevered from annular structure 40. Flexible valve leaflets 100 are attached to these posts (and elsewhere to other structure of the valve such as annular structure 40 and/or material that is used to cover structure 40). Apertures 52 through posts 50 may be used to facilitate attachment (e.g., suturing) of the leaflets to the posts. Additional apertures 54 in posts 50 may be used as sites for or to facilitate attachment of chordae tendonae (native and/or artificial replacements) to the posts. This last point will be considered further as the discussion proceeds.

The posts 50 used to attach the leaflets can be solid or can have any combination of holes and/or slots. Three independent posts 50 (i.e., "independent" because cantilevered from annular structure 40) allow for leaflet attachment, while the base 40 is secured in place as described earlier. Also, posts 50 can be lined up with the native anatomy for better leaflet opening clear of chordae and the aortic valve. Apertures 54 can be included near the downstream free ends of posts 50 for native and/or artificial chordae attachment. To mitigate leaflet abrasion at the attachment site, the stent 40 can first be covered with fabric, followed by a thin layer of buffering tissue/polymer, and finally the leaflet 100 tissue/polymer. As is true for all embodiments herein, the stent 40 of the valve can be partially or completely covered in one or a combination of materials (polyester, tissue, etc.) to allow for better in-growth, abrasion protection, sealing, and protection from metal leachables such as nickel from nitinol. The support structure 50 for the leaflets may be continuous from the clamping stent portion 40. Alternatively, the leaflet support structure may be a separate section connected to clamping portion 40, or it may be frameless.

Figure 19:
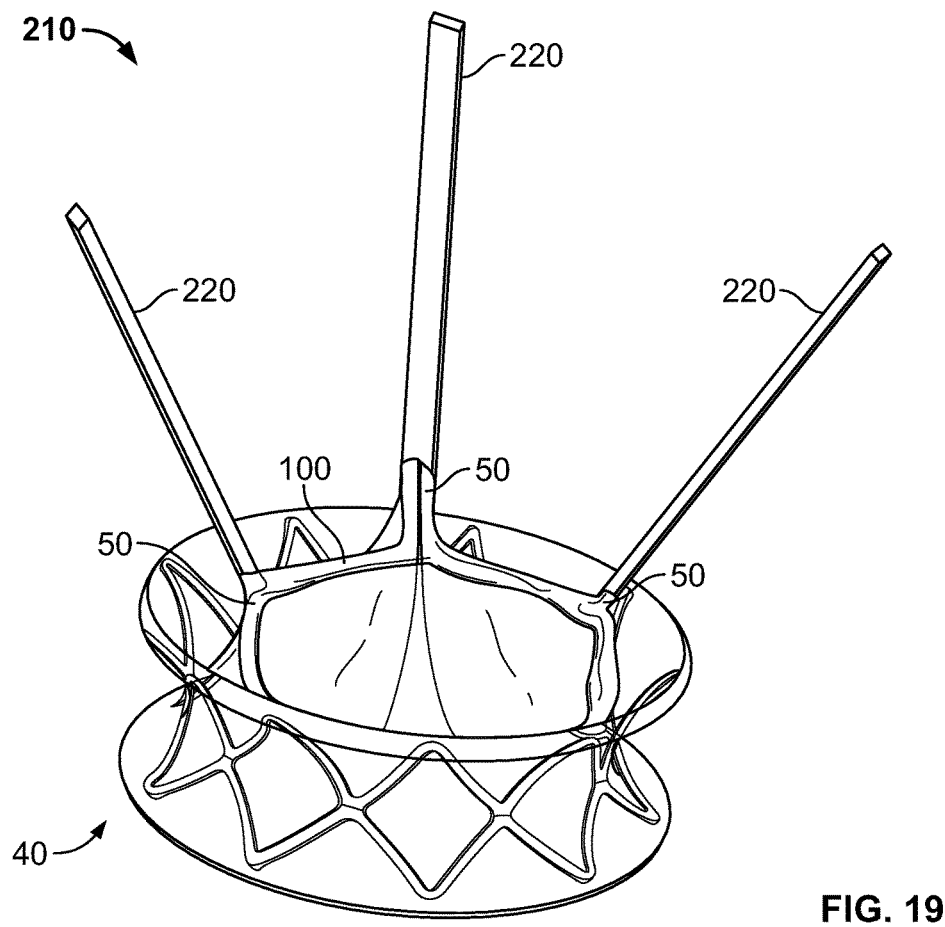
FIG. 19 is a simplified perspective view of an embodiment like that shown in FIG. 18 with other possible elements added in accordance with the invention.

FIG. 19 shows an example of how artificial and/or native chordae 220 can be attached prior to, during, or after implanting prosthetic mitral valve 210. These chordae attachments are made at or near the downstream free ends of posts 50. Chordae 220 can be adjusted through cored papillary muscles and/or through a port made in the apex of the beating heart.

Figure 20:
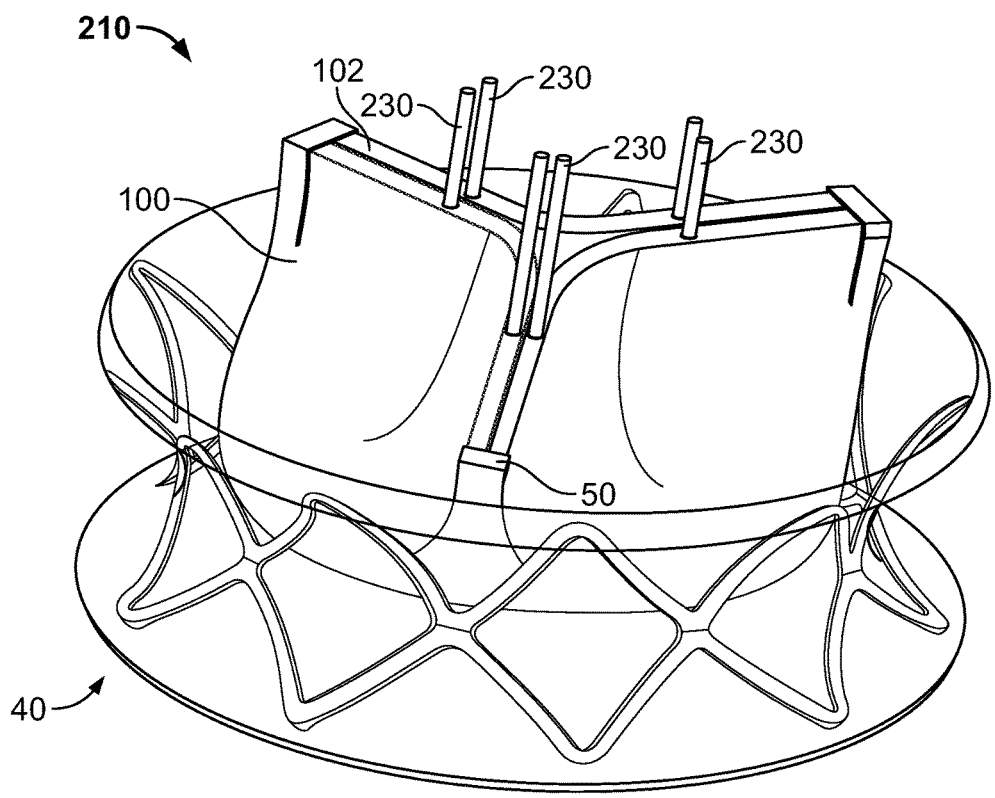
FIG. 20 is a simplified elevational view of another illustrative of a prosthetic heart valve in accordance with the invention.

FIG. 20 shows an alternative embodiment of prosthetic mitral valve 210 in which chordae 230 can be attached to an extended free edge 102 of the leaflets prior to, during, or after implanting of the valve in the patient. Once again, chordae 230 can be adjusted through cored papillary muscles and/or through a port made in the apex of the beating heart. The redundant coaptation portions 102 of the leaflets can be reinforced tissue (e.g., a double layer or thicker tissue), or if the leaflet is a polymer, it can be reinforced by greater thickness and/or fibers.

Figure 21:
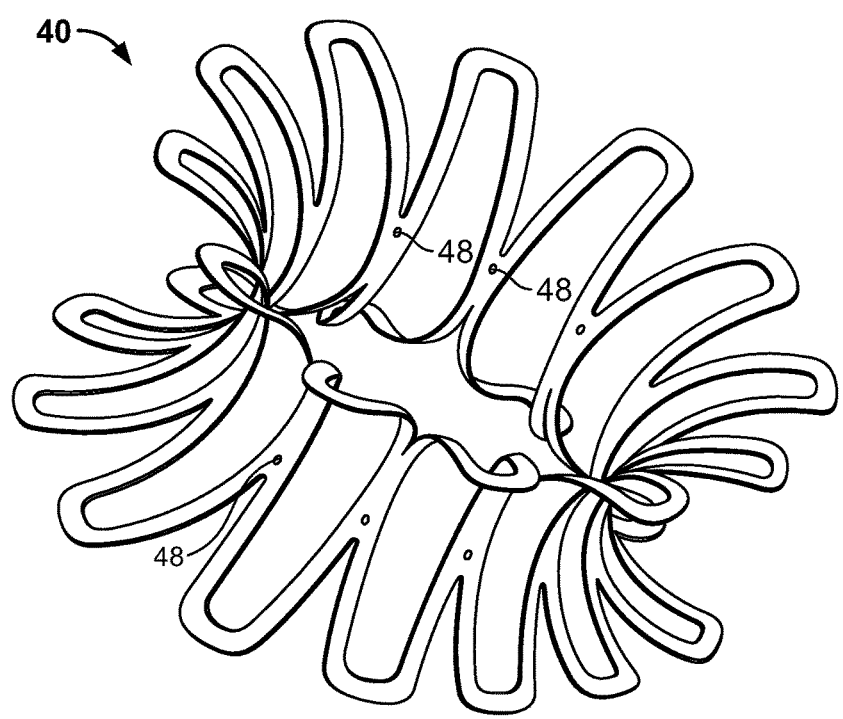
FIG. 21 is a simplified perspective view of another illustrative embodiment of a component for a prosthetic heart valve in accordance with the invention.
Figure 22:
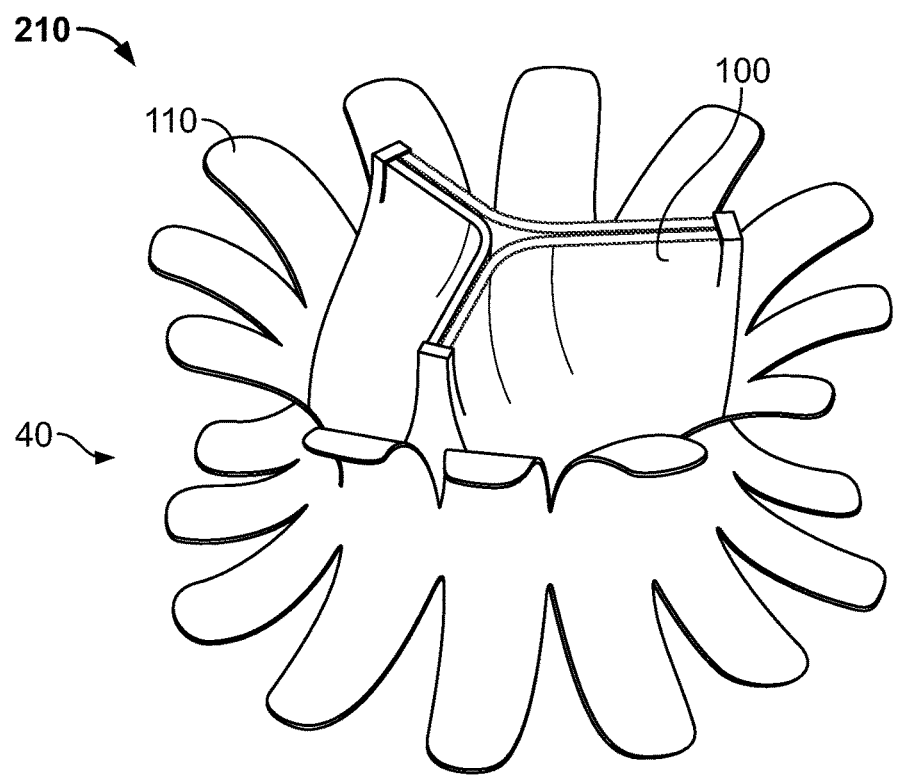
FIG. 22 is a simplified perspective view of another illustrative embodiment of a prosthetic heart valve in accordance with the invention.
Figure 23:
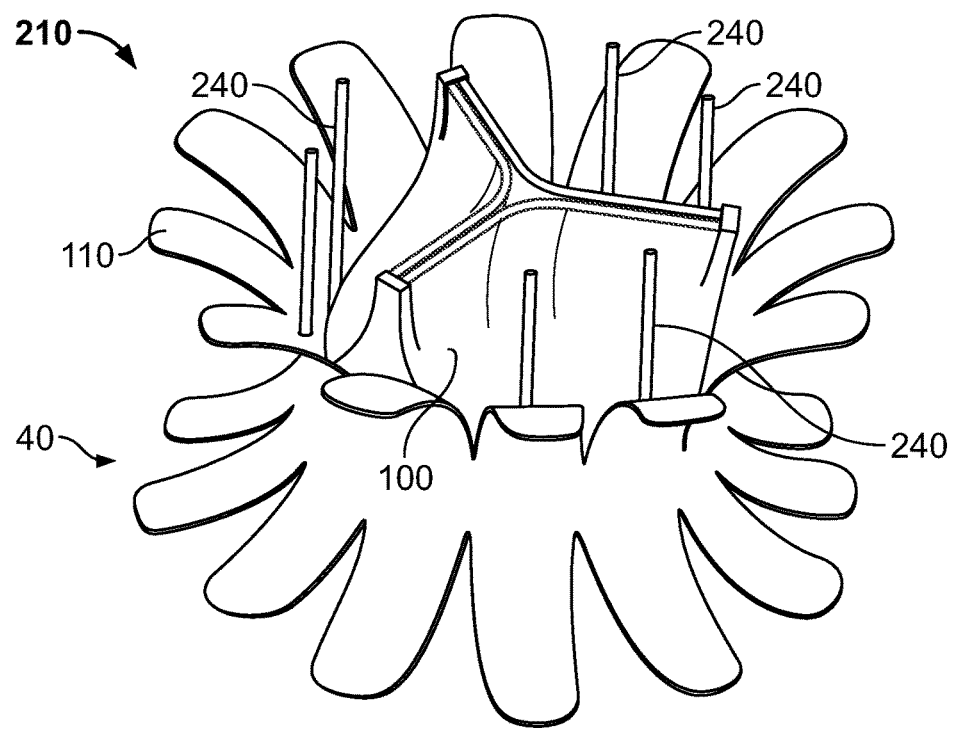
FIG. 23 is a simplified perspective view of another illustrative embodiment of a prosthetic heart valve in accordance with the invention.

FIG. 21 shows that the stent 40 design can include apertures 48 around the center portion of the stent to allow for cuff, leaflet, and chordae attachment around the circumference of the stent. FIG. 22 shows that the edge of cuff 110 can follow the edge shape of stent 40 to allow for passage of chordae and reduction of interference of other anatomy, while also allowing greater flexibility of annular structure 40. FIG. 23 shows chordae 240 extending from apertures like those shown at 48 in FIG. 21.

Figure 24:
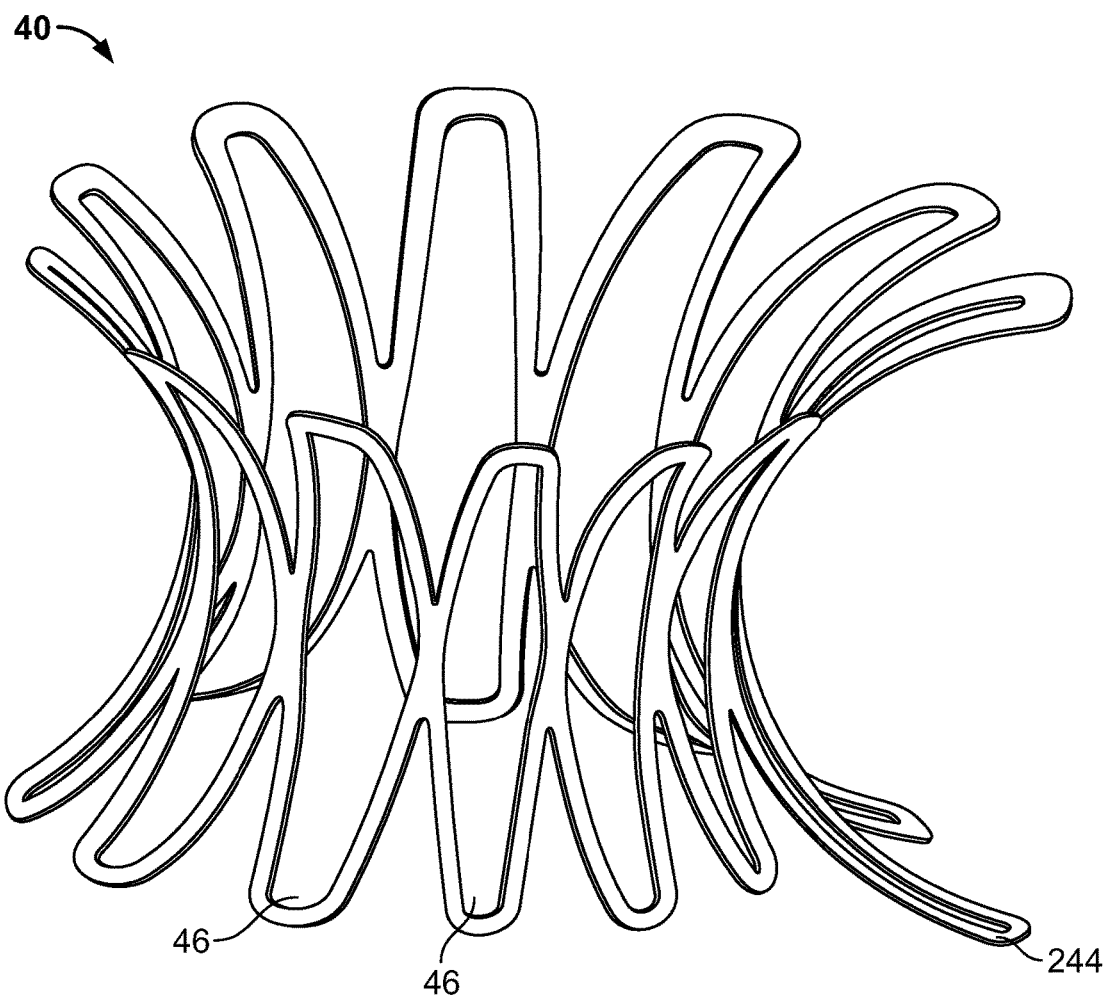
FIG. 24 is a simplified perspective view of another illustrative embodiment of a component for a prosthetic heart valve in accordance with the invention.

FIG. 24 illustrates the point that variations in stent cell 46 geometry around the circumference of annular structure 40 can reduce impingement on or of the aortic valve, chordae, and the coronary sinus. Additionally, extended portions (e.g., 244) of some cells may allow for greater holding force in certain parts of the anatomy such as in the atrial appendage.

Figure 25:
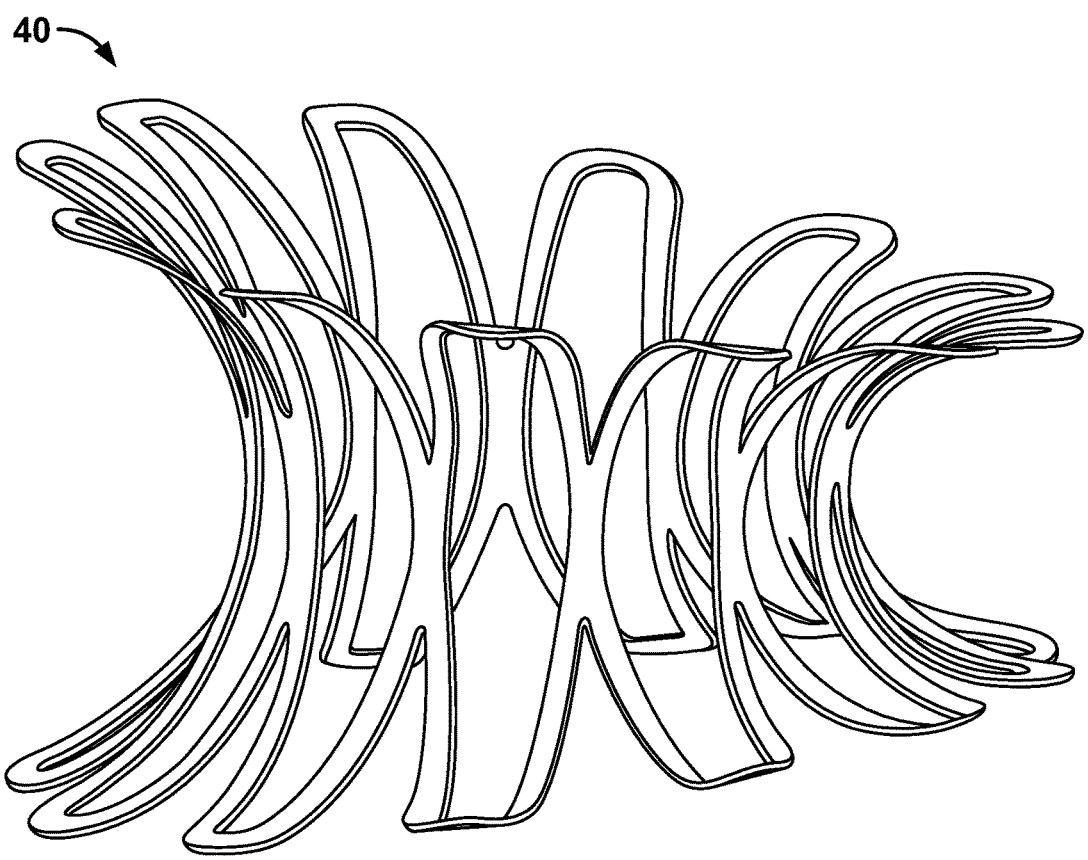
FIG. 25 is generally similar to FIG. 24 for still another illustrative embodiment of a component for a prosthetic heart valve in accordance with the invention.
Figure 26:
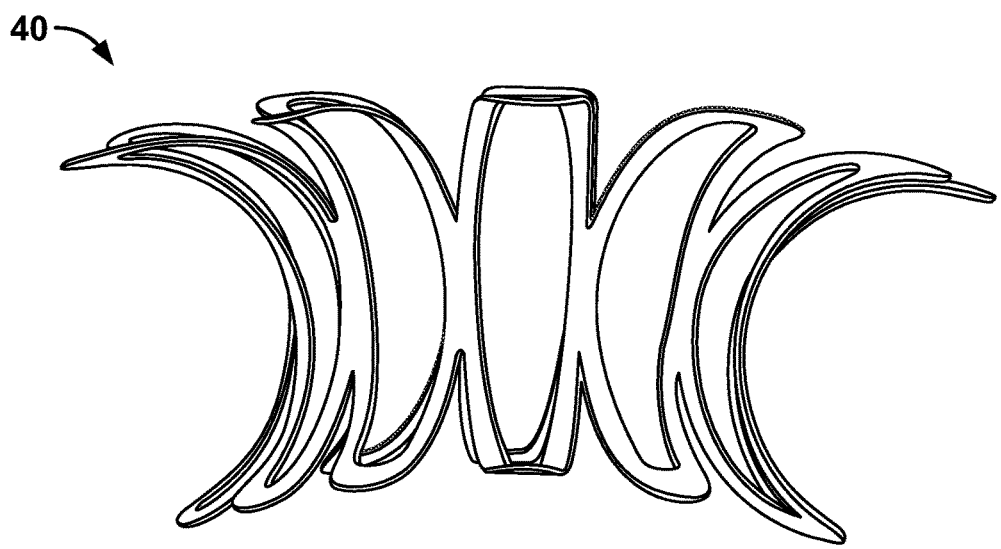
FIG. 26 is a simplified elevational view of yet another illustrative embodiment of a component for a prosthetic heart valve in accordance with the invention.

FIGS. 25 and 26 show other variations in the shape of annular structure 40 that can allow for better conformance to the mitral valve anatomy. For example, FIG. 25 shows an asymmetric shape, while FIG. 26 shows a symmetric saddle shape.

Figure 27:
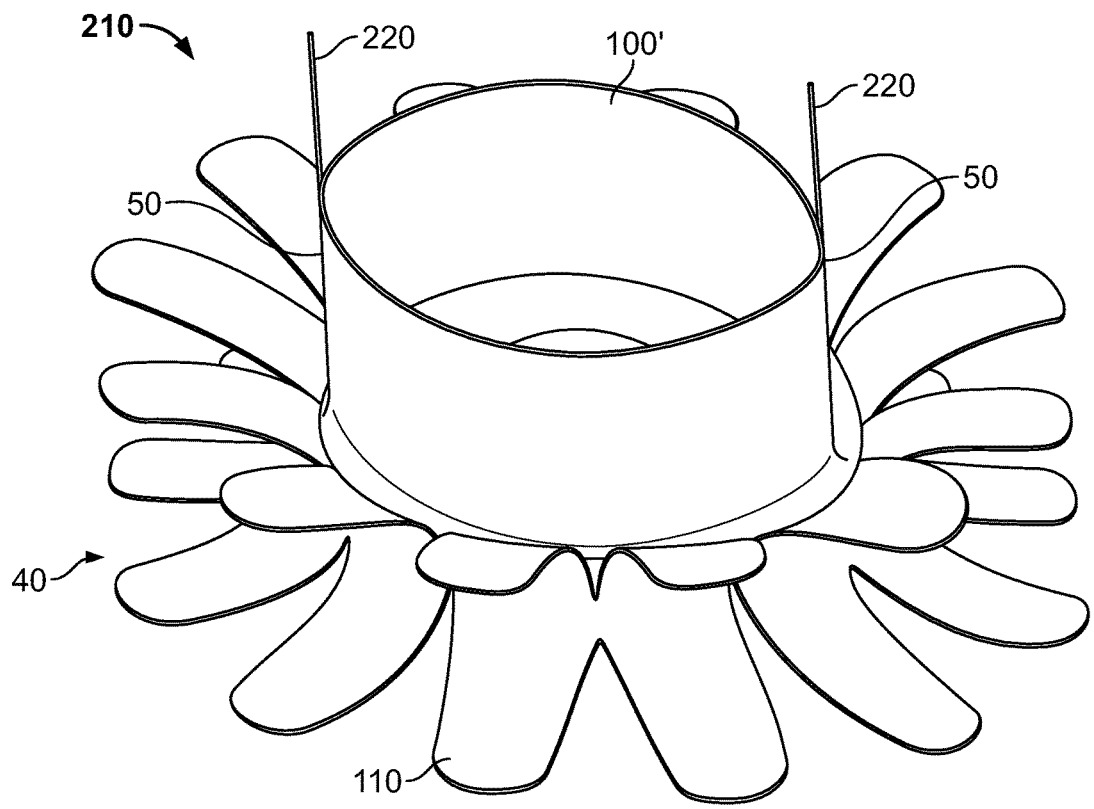
FIG. 27 is a simplified perspective view of still another illustrative embodiment of a prosthetic heart valve in accordance with the invention.

FIG. 27 shows that a valve 210 with an elliptical shape may also conform better to the mitral valve anatomy than a circular-shaped valve. Additionally, instead of a tri-leaflet design, FIG. 27 shows that a bi-leaflet design 100' can be used (leaflets shown open in FIG. 27). Once again, chordae 220 can be attached at commissure posts 50, and the edge of cuff 110 can be contoured to follow the edge of stent 40.

Although the structures shown in FIGS. 18-27 are described primarily as mitral valve structures, it will be understood that this is only illustrative, and that various structures and principles illustrated by or in these FIGS. can be employed in other types of prosthetic heart valves (e.g., in prosthetic aortic valves).

Briefly recapitulating some of what has been said in somewhat different terms, it will be seen that in many embodiments of the invention, at least the portion 40 of the prosthetic valve that goes in the patient's native valve annulus includes an annular array of generally diamond-shaped cells 46. Upstream apex portions 144 of at least some of these cells are resiliently biased to deflect radially outwardly from at least some other portions of structure 40. Downstream apex portions 142 of at least some of these cells are similarly resiliently biased to deflect radially outwardly from at least some other portions of structure 40. This allows the valve to clamp tissue of the patient between the upstream and downstream apex portions that thus deflect outwardly.

Each of the above-mentioned apex portions comprises two spaced-apart members that join at an apex of that apex portion. For example, in FIG. 7 the two spaced-apart members of one representative downstream apex portion are identified by reference letters b and c, and the apex where those members join is identified by reference letter a.

Still more particularly, the resiliently biased, radially outward deflection of each upstream apex portion 144 typically includes a downstream component of motion of that upstream apex portion (in addition to a radially outward component of motion). This is illustrated, for example, by the arcuate arrows 44 in FIGS. 1-3. Similarly, the resiliently biased, radially outward deflection of each of downstream apex portion 142 typically includes an upstream component of motion of that downstream apex portion (in addition to a radially outward component of motion). This is illustrated, for example, by the arcuate arrows 42 in FIGS. 1-3. The result of this is that the upstream and downstream apex portions begin as jaws that are relatively far apart and wide open. They then effectively pivot toward one another to clamp tissue therebetween.

References herein to an annular perimeter of a structure being changeable in length mean that the perimeter increases or decreases in size without going through any major topological change. In other words, the shape of the structure remains basically the same, and only the perimeter size changes. For example, the shape may be always basically circular. There is no folding or wrapping of the structure to change its perimeter size. The shape either basically shrinks down or expands out. A minor exception to the foregoing is that ellipses and circles are regarded herein as having the same basic topology. Thus an ellipse may shrink to a circle, for example, without that constituting "a major topological change."

It will be understood that the foregoing is only illustrative of the principles of the invention, and that various modifications can be made by those skilled in the art without departing from the scope and spirit of the invention. For example, the particular patterns of stent cells like 22 and 46 shown herein are only illustrative, and many other stent configurations can be used instead if desired. It will be appreciated that the valves of this invention can, if desired, be implanted in a patient less invasively. For example, the valves of this invention can be implanted percutaneously, trans-apically, or surgically, and with or without resected and/or debrided leaflets. Depending on the embodiment, the valve can be collapsed in a variety of configurations before deployment in a single- or multi-stage process. Access can be achieved, for example, through the femoral artery, abdominal aorta, or the apex of the heart.

The invention claimed is:

1. A prosthetic heart valve, comprising
a stent extending in a longitudinal direction between an inflow end and an outflow end and having a length from the inflow end to the outflow end;
a valve element mounted within the stent; and
a skirt connected to the stent, the skirt having an inside wall overlapping in the longitudinal direction with the valve element, an outside wall, and a space between the inside wall and the outside wall, the inside wall having a first length in the longitudinal direction less than the length of the stent such that an outflow end of the inside wall is positioned at a spaced distance from the outflow end of the stent and the outside wall having a second length in the longitudinal direction less than the first length.

2. The prosthetic heart valve as claimed in claim 1, wherein the stent has an expanded condition and a collapsed condition, the outside wall of the skirt being adapted to move radially outward into engagement within a native valve annulus to impede paravalvular leakage.

3. The prosthetic heart valve as claimed in claim 1, wherein the inside wall of the skirt is disposed around the outside of the inflow end of the stent.

4. The prosthetic heart valve as claimed in claim 1, wherein the stent is self-expanding.

5. The prosthetic heart valve as claimed in claim 1, wherein the stent is balloon expandable.

6. The prosthetic heart valve as claimed in claim 1, wherein the stent has a first portion adjacent the inflow end of the stent and a second portion adjacent the outflow end of the stent, the first portion of the stent in an expanded condition having a first diameter and the second portion of the stent in the expanded condition having a second diameter larger than the first diameter.

7. The prosthetic heart valve as claimed in claim 6, wherein the first portion of the stent is sized and shaped for implantation in a native aortic valve annulus of a patient.

8. The prosthetic heart valve as claimed in claim 1, wherein the skirt is positioned at the inflow end of the stent.

9. The prosthetic heart valve as claimed in claim 8, wherein the skirt is positioned at a spaced distance from an inflow edge of the stent.

10. The prosthetic heart valve as claimed in claim 1, wherein the valve element has a length in the longitudinal direction that is less than a length of the stent from the inflow end to the outflow end.

11. The prosthetic heart valve as claimed in claim 1, wherein the stent includes a plurality of closed cells disposed around a circumference of the stent, each of the closed cells having an area, the area of each of the closed cells at the outflow end of the stent being greater than the area of each of the closed cells at the inflow end of the stent.

12. The prosthetic heart valve as claimed in claim 1, wherein the skirt includes a polymer.

13. The prosthetic heart valve as claimed in claim 12, wherein the valve element is formed from tissue.

14. A prosthetic heart valve, comprising
a stent extending in a longitudinal direction between an inflow end and an outflow end and having a length from the inflow end to the outflow end, the stent having an expanded condition and a collapsed condition;
a valve element mounted within the stent; and
a skirt at the inflow end of the stent, the skirt including an inside wall overlapping in the longitudinal direction with the valve element and an outside wall, the inside wall having a first length in the longitudinal direction less than the length of the stent such that an outflow end of the inside wall is positioned at a spaced distance from the outflow end of the stent and the outside wall having a second length in the longitudinal direction less than the first length, the skirt being radially expandable into engagement within a native valve annulus to impede paravalvular leakage.

15. The prosthetic heart valve as claimed in claim 14, wherein in the expanded condition of the stent, the outside wall is spaced away from the stent in outward radial directions.

16. The prosthetic heart valve as claimed in claim 14, wherein in the expanded condition of the stent, the outside wall is spaced away from the inside wall in outward radial directions.

17. The prosthetic heart valve as claimed in claim 14, further comprising a fluid between the inside wall and the outside wall, the fluid spacing the outside wall away from the inside wall.

18. The prosthetic heart valve as claimed in claim 14, wherein the skirt includes a generally toroidal section having a first radial thickness and a remaining portion having a second radial thickness, the first radial thickness being greater than the second radial thickness to allow extra sealing capacity to prevent paravalvular leakage.

19. The prosthetic heart valve as claimed in claim 14, wherein the skirt is positioned at a spaced distance from an inflow edge of the stent.

20. A prosthetic heart valve, comprising
a stent extending in a longitudinal direction between an inflow end and an outflow end and having a length from the inflow end to the outflow end, the stent having an expanded condition and a collapsed condition;
a valve element mounted within the stent; and
a skirt connected to the stent, the skirt having an inside wall overlapping in the longitudinal direction with the valve element and an outside wall, the inside wall having a first length in the longitudinal direction less than the length of the stent and the outside wall having a second length in the longitudinal direction less than the first length, in the expanded condition of the stent the outside wall of the skirt being positioned at a radially outward spaced distance from the stent to provide extra sealing capacity to prevent paravalvular leakage.

21. A prosthetic heart valve, comprising
a stent extending in a longitudinal direction between an inflow end and an outflow end and having a length from the inflow end to the outflow end;
a valve element mounted within the stent; and
a skirt connected to the stent, the skirt having an inside wall overlapping in the longitudinal direction with the valve element, an outside wall and a chamber between the inside wall and the outside wall, the inside wall having a first length in the longitudinal direction less than the length of the stent such that an outflow end of the inside wall is positioned at a spaced distance from the outflow end of the stent and the outside wall having a second length in the longitudinal direction less than the first length.

22. The prosthetic heart valve as claimed in claim 21, wherein the skirt is positioned at the inflow end of the stent.

23. The prosthetic heart valve as claimed in claim 21, wherein the valve element has a length in the longitudinal direction that is less than a length of the stent from the inflow end to the outflow end.

24. The prosthetic heart valve as claimed in claim 21, wherein the stent includes a plurality of closed cells disposed around a circumference of the stent, each of the closed cells having an area, the area of each of the closed cells at the outflow end of the stent being greater than the area of each of the closed cells at the inflow end of the stent.

25. The prosthetic heart valve as claimed in claim 21, wherein the skirt includes a polymer.

26. The prosthetic heart valve as claimed in claim 25, wherein the valve element is formed from tissue.

* * * * *